(12) United States Patent
Matsushita et al.

(10) Patent No.: US 7,999,941 B2
(45) Date of Patent: Aug. 16, 2011

(54) SURFACE PLASMON RESONANCE SENSOR CHIP AND SURFACE PLASMON RESONANCE SENSOR

(75) Inventors: Tomohiko Matsushita, Kyoto (JP); Hideyuki Yamashita, Daito (JP); Takeo Nishikawa, Kyotanabe (JP); Megumi Moriyama, Ithaca, NY (US); Ryosuke Hasui, Nara (JP); Shigeru Aoyama, Kizugawa (KP)

(73) Assignee: OMRON Corporation, Kyoto (JP)

( * ) Notice: Subject to any disclaimer, the term of this patent is extended or adjusted under 35 U.S.C. 154(b) by 303 days.

(21) Appl. No.: 12/282,611

(22) PCT Filed: Mar. 14, 2007

(86) PCT No.: PCT/JP2007/055134
§ 371 (c)(1),
(2), (4) Date: Sep. 11, 2008

(87) PCT Pub. No.: WO2007/105771
PCT Pub. Date: Sep. 20, 2007

(65) Prior Publication Data
US 2010/0067015 A1 Mar. 18, 2010

(30) Foreign Application Priority Data
Mar. 15, 2006 (JP) .................................. 2006-071832

(51) Int. Cl.
*G01N 21/55* (2006.01)
(52) U.S. Cl. ...................................................... 356/445
(58) Field of Classification Search ........... 356/445–448
See application file for complete search history.

(56) References Cited

U.S. PATENT DOCUMENTS

| 6,728,429 B1* | 4/2004 | Melman et al. ................. 385/12 |
| 6,752,963 B2* | 6/2004 | Dickopf et al. ............. 422/82.09 |
| 2003/0107741 A1* | 6/2003 | Pyo et al. ....................... 356/445 |
| 2003/0113231 A1* | 6/2003 | Karube et al. ............. 422/82.05 |
| 2008/0163688 A1* | 7/2008 | Wang et al. ..................... 73/580 |

FOREIGN PATENT DOCUMENTS

JP 2001-337036 A 12/2001
(Continued)

OTHER PUBLICATIONS

International Search Report w/translation from PCT/JP2007/055134 dated May 15, 2007 (4 pages).

(Continued)

*Primary Examiner* — Michael P Stafira
(74) *Attorney, Agent, or Firm* — Osha • Liang LLP

(57) ABSTRACT

A metal layer 13 made of Au or the like is formed on the upper surface of a transparent substrate 12. Dielectric layers 14*a*, 14*b* and 14*c* with different thicknesses are formed on the upper surface of the metal layer 13 (any one of the dielectric layers can have a thickness of 0) to form respective determination areas 15*a*, 15*b* and 15*c*. Further, different types of antibodies 22*a*, 22*b* and 22*c* are fixed on the upper surfaces of the respective dielectric layers 14*a*, 14*b* and 14*c*. Then, light is directed to the determination areas 15*a*, 15*b* and 15*c*, then signals of light reflected by the determination areas 15*a*, 15*b* and 15*c* are received, the light is dispersed, and analyses are performed on signals resulted from the light dispersion to detect the conditions of the surfaces of the respective determination areas, at the same time.

22 Claims, 32 Drawing Sheets

FOREIGN PATENT DOCUMENTS

| | | |
|---|---|---|
| JP | 2002-162346 A | 6/2002 |
| JP | 2003-322610 A | 11/2003 |
| JP | 3576093 B2 | 7/2004 |
| JP | 3726772 B2 | 7/2005 |

OTHER PUBLICATIONS espacenet.com Abstract of JP2001-337036 dated Dec. 7, 2001; Karube Masao (2 pages).

espacenet.com Abstract JP2003-322610 dated Nov. 14, 2003; Omron Tateisi Electronics Co. (2 pages).

espacenet.com Abstract of JP2002-162346 dated Jun. 7, 2002; Nippon Telegraph & Telephone (2 pages).

Written Opinion from PCT/JP2007/055134 dated May 15, 2007 (3 pages).

International Preliminary Report on Patentability dated Jul. 1, 2008 (5 pages).

\* cited by examiner (a)

(b)

(a)

(b)

(a)

(b)

(c)

SURFACE PLASMON RESONANCE SENSOR CHIP AND SURFACE PLASMON RESONANCE SENSOR

TECHNICAL FIELD

The present invention relates to a surface plasmon resonance sensor chip and a surface plasmon resonance sensor. More specifically, the present invention relates to a surface plasmon resonance sensor which disperses the light of signals from a sample detection portion having a plurality of dielectric layers with different thicknesses for detecting the conditions of the surfaces of respective determination areas in the sample detection portion, a surface plasmon resonance sensor chip for use in the surface plasmon resonance sensor, and a medical inspection apparatus and a chemical-material inspection apparatus which employ the surface plasmon resonance sensor.

BACKGROUND ART

In recent years, diagnoses of health and constitutional predisposition of individual persons and foreseeing of illnesses have been increasingly enabled by inspections of genes and proteins of individual persons. As apparatuses for use therewith, there have been suggested various types of apparatuses, as will be described later. However, presently, these apparatuses have large sizes and are expensive and, in order to increase the processing efficiency for enabling performing a plurality of inspections at one time or in order to increase the determination accuracy, it has been necessary to increase the sizes of these apparatuses and to make these apparatuses more expensive. On the other hand, in order to cause these inspection apparatuses to be widely used, there has been a need for providing inexpensive apparatuses with reduced sizes and higher accuracy in the future.

Hereinafter, conventional apparatuses will be briefly described from the aforementioned perspective.

Japanese Unexamined Patent Publication Application No. 2000-131237 (Patent Document 1) suggests a fluorescence-detection type inspection apparatus. This is an apparatus for, after biomolecules are decorated with a fluorescent coloring agent, observing fluorescence emitted from the biomolecules which have specifically combined with cDNAs fixed on a slide glass. Such fluorescence-detection type inspection apparatuses enable performing analyses of a plurality of types of genes and proteins by applying different cDNAs to a slide glass in dot shapes. Accordingly, presently, such fluorescence-detection type inspection apparatuses have been widely used.

However, such inspection apparatuses induce the problem of the occurrence of errors due to fluorescent coloring agents, since they detect imperceptible fluorescence, and also induce the problem of large sizes of optical systems for fluorescence detection and, therefore, high fabrication costs.

Further, Japanese Patent Application Laid-Open Publication No. 6-167443 (Patent Document 2) suggests a bulk-type surface plasmon resonance sensor. This apparatus includes a triangular prism placed on the lower surface of a substrate, and a metal thin film formed on the upper surface of the substrate. The surface plasmon resonance sensor introduces light to the interface between the metal thin film and the prism at various angles, with a light projection optical system, and determines, with a photo detector, the intensity of the light reflected by the interface between the metal thin film and the prism. With this apparatus, it is possible to detect reactions between antibodies and the like fixed to the metal thin film and antigens which specifically combine therewith, from the change of the intensity of light received by the photo detector.

Such a bulk-type surface plasmon resonance sensor induces no error due to fluorescent molecules, but its structure is difficult to array and, accordingly, only a single inspection can be performed at one time with a single surface plasmon resonance sensor. Furthermore, conventional bulk-type surface plasmon resonance sensors have involved image processing for analyses, which has caused the surface plasmon resonance sensors to have large sizes and also has required times for analyses.

As means for reducing the sizes of surface plasmon resonance sensors, there have been suggested various types of optical-waveguide type surface plasmon resonance sensors which utilize waveguide-type surface plasmon resonance. An optical-waveguide type surface plasmon resonance sensor includes a core embedded in a clad layer and a metal thin film provided on the upper surface of the core, such that light is introduced to the core from its one end and the light emitted from the other end of the core is received by a photo detector.

JP-A. No. 2002-162346 (Patent Document 3) discloses such optical-waveguide type surface plasmon resonance sensors. This Document describes a structure having a single core and a structure having a plurality of cores formed in parallel by branching a core and providing a switching portion on the core. The structure having a single core enables providing only a single metal thin film therein, which makes it impossible to perform a plurality of inspections at one time.

Further, the structure having the plurality of cores enables providing metal thin films on the respective cores for performing a plurality of inspections at one time, but only a single core can be provided on each core. Accordingly, the number of metal thin films can not be made greater than the number of cores, and it is necessary to increase the number of cores and the number of switching portions, in order to increase the number of metal thin films. Furthermore, in order to branch the core in a plurality of stages, it is necessary to increase the area of the branched portion of the core, thereby increasing the size of the surface plasmon resonance sensor. Accordingly, such a surface plasmon resonance sensor having a plurality of cores has had the problem of the necessity of significantly increasing the size of the sensor in order to enable performing a plurality of inspections.

[Patent Document 1] JP-A. No. 2000-131237
[Patent Document 2] JP-A. No. 6-167443
[Patent Document 3] JP-A. No. 2002-162346

DISCLOSURE OF THE INVENTION

Problems to be Solved by the Invention

The present invention was made in view of the aforementioned circumstances and aims at providing a surface plasmon resonance sensor and a surface plasmon resonance sensor chip having small sizes and high accuracy which are capable of dispersing the light of signals from a sample detection portion having a plurality of dielectric layers with different thicknesses (hereinafter, light reflected by the sample detection portion may be referred to as signals) for detecting the conditions of the surfaces of respective determination areas.

Means for Solving the Problems

A first surface plasmon resonance sensor chip according to the present invention is characterized to include a substrate; a metal layer formed on the upper surface of the substrate; and a plurality of dielectric layers formed on the aforementioned metal layer; wherein at least portions of the aforementioned plurality of dielectric layers have thicknesses different from one another (including a thickness of 0). Further, a dielectric layer having a thickness of 0 means no dielectric layer.

In the first plasmon resonance sensor chip according to the present invention, the dielectric layers with different thicknesses are formed on the metal layer, which can separate the characteristic wavelengths of signals (reflected light) obtained from the respective dielectric layers (determination areas) from one another. This can prevent the characteristic wavelengths of the signals obtained from the respective dielectric layers from overlapping with one another, thereby enabling determinations of small amounts of chemical changes, biological changes or physical changes in the respective determination areas. Accordingly, with the surface plasmon resonance sensor chip according to the present invention, it is possible to perform a plurality of inspections at one time. Furthermore, it is possible to fabricate a surface plasmon resonance sensor chip with a reduced size and lower cost.

In an embodiment of the surface plasmon resonance sensor chip according to the present invention, a plurality of metal layers are placed such that they are spaced apart from one another by a predetermined distance, wherein the dielectric layers are formed on the respective metal layers. In the embodiment, there are sets of metal layers and dielectric layers, which prevent the metal layers from being exposed through the dielectric layers. This enables applying hydrophilic processing or hydrophobic processing to the upper surface of the substrate for suppressing non-specific adhesion of samples to the upper surface of the substrate, which reduces signal noises due to samples adhered to the upper surface of the substrate, thereby increasing the determination accuracy of the surface plasmon resonance sensor chip.

In another embodiment of the surface plasmon resonance sensor chip according to the present invention, a prism is intimately contacted with the lower surface of the substrate. In the embodiment, the surface plasmon resonance sensor chip can have so-called Kretschmann placement.

In another embodiment of the surface plasmon resonance sensor chip according to the present invention, there are provided a plurality of sample detection portions including a plurality of dielectric layers having different thicknesses formed on the upper surface of the metal layer. In the case of providing a plurality of sample detection portions, even when there are dielectric layers with the same thickness in different sample detection portions, the light reflected by the respective sample detection portions can be dispersed, and the dispersed light can be received by the plurality of light receiving devices or can be received in order by the plurality of light receiving devices in a time sequential manner, which enables determinations with the respective determination areas, thereby enabling performing a greater number of determinations at one time. Furthermore, with this embodiment, it is possible to reduce the thickness difference in the supporting surface, thereby facilitating the fabrication of the surface plasmon resonance sensor chip.

A first surface plasmon resonance sensor according to the present invention is characterized to include the first surface plasmon resonance sensor chip having the prism intimately contacted with the lower surface of the substrate according to the present invention; a light source placed such that light enters the prism from one of the inclined surfaces of the prism; and a light dispersion means and a light receiving device placed such that the light emitted from the other inclined surface of the prism reaches the light dispersion means and the light receiving device; wherein the light emitted from the light source and entered the prism is reflected by the interface between the substrate and the metal layer, the light reflected by the interface is dispersed by the light dispersion means, and the light with different wavelengths resulted from the light dispersion by the light dispersion means is received by a plurality of light receiving areas of the light receiving device.

In the first plasmon resonance sensor according to the present invention, the dielectric layers with different thicknesses are formed on the metal layer, which can separate the characteristic wavelengths of signals (reflected light) obtained from the respective dielectric layers (the determination areas) from one another. This can prevent the characteristic wavelengths of the signals obtained from the respective dielectric layers from overlapping with one another. Accordingly, by dispersing the light reflected by the sample detection portion through the light dispersion means and detecting the shifts of the characteristic wavelengths or by projecting, in order, monochromatic light with different wavelengths to the sample detection portion and detecting the shifts of the characteristic wavelengths, it is possible to determine small amounts of chemical changes, biological changes or physical changes in the respective determination areas. Accordingly, with the surface plasmon resonance sensor according to the present invention, it is possible to perform a plurality of inspections at one time. Furthermore, it is possible to fabricate a surface plasmon resonance sensor with a reduced size and lower cost. Furthermore, with the aforementioned surface plasmon resonance sensor, light with a certain wavelength range (for example, while light) reflected by the determination areas can be dispersed, through the light dispersion means such as a grating, and, from the wavelength spectra resulted therefrom, the shifts of characteristic wavelengths can be detected, at one time. This can increase the speed of determination operations in comparison with the method for projecting, in order, monochromatic light with different wavelengths to the sample detection portion and detecting the shifts of characteristic wavelengths. Furthermore, there is no need for using a CCD as a light receiving device, thereby eliminating the necessity of image processing and also reducing the time required for analyses of the results of determinations.

A second surface plasmon resonance sensor chip according to the present invention is characterized to include an optical waveguide having a core formed therein; determination areas formed on the core; and a light dispersion means for dispersing light which has been propagated through the core and reflected by the determination areas; wherein the determination areas include a metal layer formed on the core, and a plurality of dielectric layers formed on the metal layer, and at least portions of the plurality of dielectric layers have thicknesses different from one another (including a thickness of 0). Further, a dielectric layer having a thickness of 0 means no dielectric layer. In the determination areas provided with dielectric layers, a material capable of recognizing a certain molecule and specifically combining therewith (hereinafter, referred to as a molecule-recognition-function material) is fixed to the dielectric layers, but, in the determination areas provided with no dielectric layer, a molecule-recognition-function material is directly fixed to the metal layer. Accordingly, the determination areas are defined by the areas to which the molecule-recognition-function material is fixed (the same applies to the following description).

With the second plasmon resonance sensor chip according to the present invention, the dielectric layers with different thicknesses are formed along the upper surface of the core, which can separate the characteristic wavelengths of signals (reflected light) obtained from the respective dielectric layers (the determination areas) from one another. This can prevent the characteristic wavelengths of the signals obtained from the respective dielectric layers from overlapping with one another. Accordingly, by dispersing the light reflected by the sample detection portion through the light dispersion means and detecting the shifts of the characteristic wavelengths, it is possible to determine small amounts of chemical changes, biological changes or physical changes in the respective determination areas. Accordingly, with the second surface plasmon resonance sensor chip according to the present invention, it is possible to perform a plurality of inspections at one time. Furthermore, it is possible to fabricate a surface plasmon resonance sensor chip with a reduced size and lower cost.

In an embodiment of the second surface plasmon resonance sensor chip according to the present invention, there are provided a plurality of metal layers placed such that they are spaced apart from one another by a predetermined distance, wherein the dielectric layers are formed on the respective metal layers. In the embodiment, there are sets of metal layers and dielectric layers, which prevent the metal layer from being exposed through the dielectric layers. This enables applying hydrophilic processing or hydrophobic processing to the upper surface of the core for suppressing non-specific adhesion of samples to the upper surface of the core, which reduces signal noises due to samples adhered to the upper surface of the core, thereby increasing the determination accuracy of the surface plasmon resonance sensor chip.

In another embodiment of the second surface plasmon resonance sensor chip according to the present invention, the optical waveguide includes a plurality of cores formed therein, and the determination areas are formed on the respective cores. In the embodiment, the number of determination areas is further increased with increasing number of cores, which can further increase the types of determinations which can be performed at one time and the number of samples.

In another embodiment of the second surface plasmon resonance sensor chip according to the present invention, the length D of the respective dielectric layers in the core longitudinal direction is expressed as follows, $$D \geq 2 \times T \times \tan \theta$$

wherein T is a thickness of the core, and $\theta$ is the incidence angle at which light propagated through the core enters the determination areas. In this embodiment, it is possible to define the minimum necessary length of the dielectric layers (the determination areas) with respect to the thickness of the core, which facilitates designing of the surface plasmon resonance sensor chip.

In another embodiment of the second surface plasmon resonance sensor chip according to the present invention, the light dispersion means is provided at a portion of the core, and there is provided a light receiving device including a plurality of light receiving areas which receive light with different wavelengths resulted from the light dispersion by the light dispersion means. By providing the light receiving device which receives light with different wavelengths resulted from the light dispersion means, it is possible to detect easily the changes of characteristic wavelengths of signals, thereby easily performing analyses of samples and characteristics thereof.

In another embodiment of the first or second surface plasmon resonance sensor chip according to the present invention, different molecule-recognition-function materials are fixed to the respective determination areas. In the embodiment, different molecule-recognition-function materials are fixed to the respective determination areas, which enables performing determinations on a plurality of types of materials at the same time, thereby efficiently performing determinations.

In another embodiment of the first or second surface plasmon resonance sensor chip according to the present invention, the dielectric layers have thicknesses different from one another by 10 nm or more. The core, the metal layer and the dielectric layers are usually made of PMMA (Polymethyl Methacrylate), Au and $Ta_2O_5$, respectively, and, in this case, when normal biomolecules have been adhered, if the thickness difference between dielectric layers is 100 nm or more, the characteristic wavelengths of signals are 100 nm or more, thereby detecting the characteristic wavelengths of signals from one other with higher accuracy.

In another embodiment of the first or second surface plasmon resonance sensor chip according to the present invention, the metal layer is made of Au, Ag or Cu. In the embodiment, the metal layer is made of Au, Ag or Cu, which enables efficiently obtaining surface plasmon resonance signals within a visible light range.

In another embodiment of the first or second surface plasmon resonance sensor chip according to the present invention, the dielectric layers are made of a material with a high dielectric constant. By forming the dielectric layers from a material with a high dielectric constant, in the case of separating the characteristic wavelengths of signals from one another by the same interval, it is possible to reduce the thickness difference among dielectric layers (particularly, the difference between the maximum thickness and the minimum thickness of the dielectric layers), thereby reducing the concavity and convexity of the surface of the surface plasmon resonance sensor chip. Accordingly, with the embodiment, it is possible to facilitate the fabrication of the dielectric layers, thereby suppressing the occurrence of defects, such as chips, in the dielectric layers. Further, it is possible to reduce the pitch of the dielectric layers, thereby increasing the density of the placement of the determination areas.

In another embodiment of the first or second surface plasmon resonance sensor chip according to the present invention, the dielectric layers, which are a material with a high dielectric constant, are made of $Ta_2O_5$ or $TiO_2$. Since $Ta_2O_5$ and $TiO_2$ are materials with a high dielectric constant, in the case of separating the characteristic wavelengths of signals from one another by the same interval, it is possible to reduce the thickness difference among the dielectric layers (particularly, the difference between the maximum thickness and the minimum thickness of the dielectric layers), thereby reducing the concavity and convexity of the surface of the surface plasmon resonance sensor chip. Accordingly, with the embodiment, it is possible to facilitate the fabrication of the dielectric layers, thereby suppressing the occurrence of defects, such as chips, in the dielectric layers. Further, it is possible to reduce the pitch of the dielectric layers, thereby increasing the density of the placement of the determination areas. Further, $Ta_2O_5$ and $TiO_2$ are easily available.

In another embodiment of the first or second surface plasmon resonance sensor chip according to the present invention, the dielectric layers are made of a resin with a high refractive index. By forming the dielectric layers from a resin with a high refractive index, in the case of separating the characteristic wavelengths of signals from one another by the same interval, it is possible to reduce the thickness difference among the dielectric layers (particularly, the difference between the maximum thickness and the minimum thickness of the dielectric layers), thereby reducing the concavity and convexity of the surface of the surface plasmon resonance sensor chip. Accordingly, with the embodiment, it is possible to facilitate the fabrication of the dielectric layers, thereby suppressing the occurrence of defects, such as chips, in the dielectric layers. Further, by using a resin material, it is possible to fabricate, easily, the dielectric layers to be used in a surface plasmon resonance sensor chip, through replication using a die.

A second surface plasmon resonance sensor according to the present invention is characterized to include the second surface plasmon resonance sensor chip according to the present invention; a light source provided near one end surface of the core; an optical-path changing means provided between the light source and the core; a light dispersion means provided at a portion of the core; and a light receiving device; wherein the light emitted from the light source is adjusted to have a predetermined angle by the optical path changing means and then is introduced to the core, the light propagated through the core is reflected by the determination areas, the light emitted from the core is dispersed by the light dispersion means, and the dispersed light is received by the light receiving device.

If the light directed to the determination areas has a divergence angle, this will cause errors corresponding to the divergence angle in signals. On the contrary, with the second surface plasmon resonance sensor according to the present invention, it is possible to suppress the divergence of the light directed to the sample detection portion by the optical-path changing means. Accordingly, with the second surface plasmon resonance sensor, it is possible to further improve the determination accuracy, in addition to the effects of the second surface plasmon resonance sensor chip.

In an embodiment of the first or second surface plasmon resonance sensor according to the present invention, the light source is a white light source or a multi-wavelength light source. In the embodiment, it is possible to direct light with a greater wavelength range to the sample detection portion using a while light source or a multi-wavelength light source, thereby increasing the number of determination areas.

In an embodiment of the first or second surface plasmon resonance sensor according to the present invention, characteristic wavelengths of light reflected by the interface between the substrate and the metal layer in the areas in which the respective dielectric layers are placed are separated from one another by 100 nm or more. The substrate or core, the metal layer and the dielectric layers are usually made of PMMA (Polymethyl Methacrylate), Au and $Ta_2O_5$, respectively, and, in this case, when normal biomolecules have been adhered, the characteristic wavelengths of signals are shifted by about 50 nm. Accordingly, by separating the characteristic wavelengths (absorption wavelength ranges in which the refractivity is minimized) of signals from one another by 100 nm or more as in the present embodiment, it is possible to detect the characteristic wavelengths of signals with high accuracy.

A first method for fabricating a surface plasmon resonance sensor chip according to the present invention is a method for fabricating the first or second surface plasmon resonance sensor chip, wherein a dielectric resin material is provided on the metal layer, and then the dielectric resin material is pressed by a die having a plurality of concave portions with different depths formed therein to form a plurality of dielectric layers having different thicknesses from the dielectric resin material. With the first fabrication method which shapes a dielectric resin material (particularly, a UV-curable resin) using a die (stamper), it is possible to fabricate fine dielectric layers with higher accuracy, thereby increasing the density of the determination areas or reducing the size of the surface plasmon resonance sensor chip.

A second method for fabricating a surface plasmon resonance sensor chip according to the present invention is a method for fabricating the first or second surface plasmon resonance sensor chip according to the present invention, the method including the steps of: providing a dielectric resin material on the metal layer, and pressing the dielectric resin material by a die having a plurality of concave portions with different depths formed therein to form a plurality of dielectric layers having different thicknesses from the dielectric resin material; and removing, through etching, the portions of the metal layer which are exposed through the dielectric layers. With the second fabrication method which shapes a dielectric resin material (particularly, a UV-curable resin) using a die (stamper), it is possible to fabricate fine dielectric layers with higher accuracy, thereby increasing the density of the determination areas or reducing the size of the surface plasmon resonance sensor chip. Further, by applying etching to the metal layer using the dielectric layers as a mask, it is possible to remove easily the portions of the metal layer which are exposed through the dielectric layers.

A medical inspection apparatus according to the present invention includes the first or second surface plasmon resonance sensor according to the present invention including a biomolecule-recognition-function material which combine with a certain biomolecule and is fixed on the dielectric layers, and means for performing analyses of the results of inspections on the basis of wavelength spectra of determination light obtained by the surface plasmon resonance sensor. With the medical inspection apparatus according to the present invention, it is possible to perform a plurality of medical inspections at the same time while reducing the size thereof.

A chemical-material inspection apparatus according to the present invention includes the first or second surface plasmon resonance sensor according to the present invention including a chemical-material-recognition-function material which combines with a certain chemical material and is fixed on the dielectric layers, and means for performing analyses of the results of inspections on the basis of wavelength spectra of determination light obtained by the surface plasmon resonance sensor. With the chemical-material inspection apparatus according to the present invention, it is possible to perform a plurality of chemical-material inspections at the same time while reducing the size thereof.

Further, the means for solving the problems of the present invention has characteristics which are combinations of the components, and various types of variations can be made to the present invention by combining these components.

DESCRIPTION OF REFERENCE CHARACTERS

Figure 1:
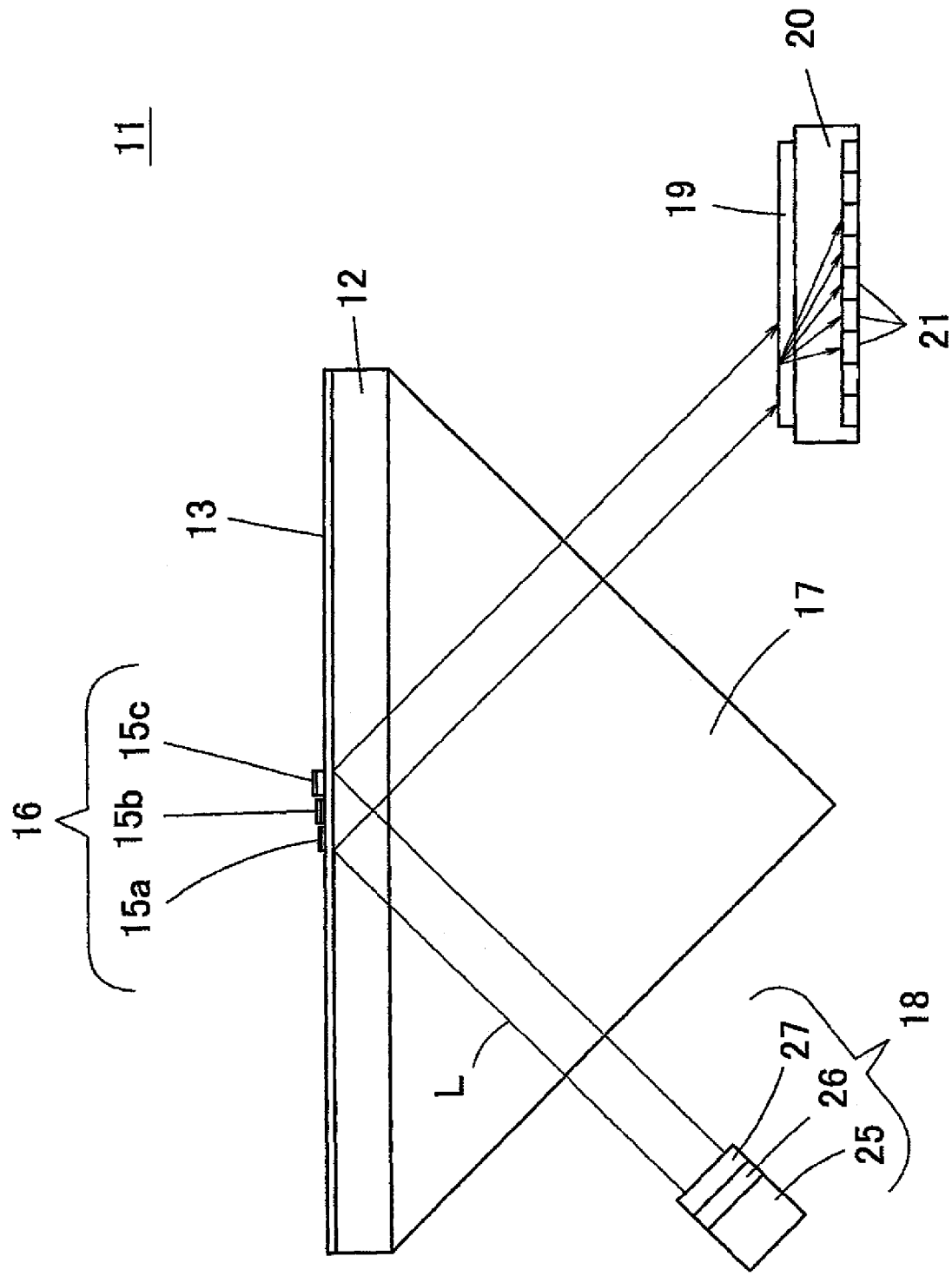
FIG. 1 is a schematic view illustrating a surface plasmon resonance sensor 11 according to a first example.

11: surface plasmon resonance sensor
12: transparent substrate
13: metal layer
14a, 14b and 14c: dielectric layers
15a, 15b and 15c: determination areas
16: sample detection portion
17: prism
18: light projection portion
19: light dispersion means
20: light receiving device
21: light receiving area
22a, 22b and 22c: antibodies
23: interval
24: antigen
25: light source
26: polarizer
27: collimate optical system
61: surface plasmon resonance sensor
62: clad
63: core

BEST MODE FOR CARRYING OUT THE INVENTION

Hereinafter, examples of the present invention will be described in detail, with reference to the drawings.

FIRST EXAMPLE

FIG. 1 is a schematic view illustrating a surface plasmon resonance sensor 11 according to the first example. The surface plasmon resonance sensor 11 according to the first example is a bulk-type surface plasmon resonance sensor including a prism 17 and employs so-called Kretschmann placement.

The surface plasmon resonance sensor 11 includes a transparent substrate 12 made of a plastic such as PMMA, polycarbonate (PC) or polystyrene (PS) or a glass, and a metal layer 13 (metal thin film) formed on the entire surface of the transparent substrate 12. The transparent substrate 12 has a refractive index equal to that of the prism 17. The metal layer 13 is made of Au, Ag, Cu and the like formed on the upper surface of the transparent substrate 12 by vacuum deposition or sputtering.

Figure 2:
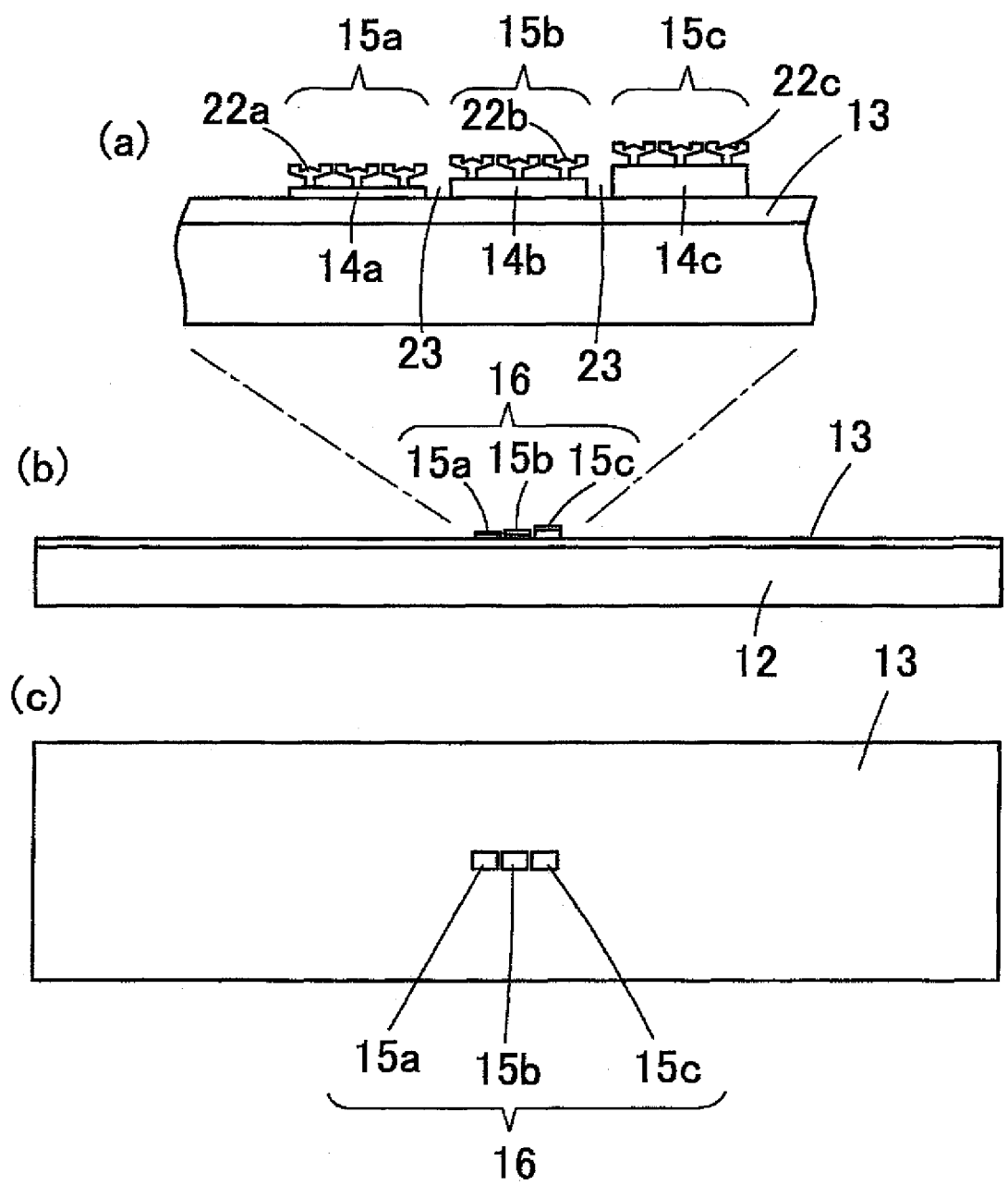
FIG. 2(a) is an enlarged view of a sample detection portion according to the first example.
FIG. 2(b) and FIG. 2(c) are a side view and a plan view of the sample detection portion.

On the upper surface of the metal layer 13, there is formed a sample detection portion 16 constituted by a plurality of determination areas 15a, 15b, 15c. FIG. 2(a) is an enlarged view of the sample detection portion 16, and FIG. 2(b) and FIG. 2(c) are a side view and a plan view of the sample detection portion 16. The determination areas 15a, 15b and 15c constituting the sample detection portion 16 are arranged in a line and are spaced apart from one another by an interval 23. In the determination area 15a, a dielectric layer 14a is formed on the upper surface of the metal layer 13, and an antibody 22a is fixed on the dielectric layer 14a. In the determination area 15b, a dielectric layer 14b having a thickness different from that of the dielectric layer 14a is formed on the upper surface of the metal layer 13, and an antibody 22b different from that in the determination area 15a is fixed on the dielectric layer 14b. In the determination area 15c, a dielectric layer 14c having a thickness different from those of the dielectric layers 14a and 14b is formed on the upper surface of the metal layer 13, and an antibody 22c different from those in the determination areas 15a and 15b is fixed on the dielectric layer 14c. Further, in the figure, there are illustrated the three determination areas 15a, 15b and 15c, but the number of determination areas can be 2 or 4 or more. Further, it is necessary only that the dielectric layers 14a, 14b and 14c have different thicknesses and, also, any of the dielectric layers (for example, the dielectric layer 14a) can have a thickness of 0 (namely, no dielectric layer can be provided). These dielectric layers 14a, 14b and 14c are made of a material with a high dielectric constant such as $Ta_2O_5$ or $TiO_2$ or a dielectric resin material having a high refractive index such as PMMA or polycarbonate.

The areas of the dielectric layers 14a, 14b and 14c (any of the determination areas can have no dielectric layer) formed on the metal layer 13 form the respective determination area 15a, 15b and 15c, and the determination areas 15a, 15b and 15c including the dielectric layers having different thicknesses (including a thickness of 0) collectively form the single sample detection portion 16.

As illustrated in FIG. 1, the transparent 12 is intimately contacted with the upper surface of the prism 17 made of a triangle prism or the like, with a matching oil formed thinly on the lower surface the transparent substrate 12. Near one of the inclined surfaces of the prism 17, there is placed a light projection portion 18 such as a white light source for emitting white light and a multi-wavelength light source for emitting light in a plurality of predetermined wavelength ranges. The light projection portion 18 includes a light source 25 such as a light emitting diode (LED), a semiconductor laser device (LD) or a halogen lamp, a polarizer 26 which converts light emitted from the light source 25 into linear polarized light in the direction parallel or perpendicular to the metal layer 13, and a collimate optical system 27 for collimating the light emitted from the light projection portion 18 and emitting the collimated light in a predetermined direction. Further, near the other inclined surface of the prism 17, there are placed a light dispersion means 19 and a light receiving device 20. The light dispersion means 19 disperses the light completely reflected by the interface between the transparent substrate 12 and the metal layer 13 and is constituted by a diffraction grating. The light receiving device 20 includes a plurality of light receiving areas 21 (light receiving cells) which receive dispersed light with different wavelengths and is constituted by a one-dimensional photodiode array or the like.

Thus, in the surface plasmon resonance sensor 11, the light L (polarized light) emitted from the light projection portion 18 enters the prism 17 at its one inclined surface, then passes through the transparent substrate 12 and diagonally enters the sample detection portion 16. Then, the light is completely reflected by the interface between the metal layer 13 and the transparent substrate 12 in the sample detection portion 16, then passes through the transparent substrate 12 and the prism 17 and exits the prism 17 to the outside from the other inclined surface of the prism 17. The light exited the prism 17 enters diagonally the light dispersion means 19 and passes through the light dispersion means 19 to be dispersed into light with different wavelengths. The respective lights with different wavelengths resulted from the light dispersion by the light dispersion means 19 are emitted in different directions and are received by the light receiving device 20. The light receiving areas 21 in the light receiving device 20 are arranged in the direction of the light dispersion by the light dispersion means 19, and the respective light receiving areas 21 receive light with different wavelengths. This enables determining spectral characteristics of the light reflected by the sample detection portion 16 from the amounts of light received by the respective light receiving areas 21.

Further, the determination areas 15a, 15b and 15c are placed such that they are spaced apart from one another by a certain distance, which causes the lights completely reflected by the respective determination areas 15a, 15b and 15c to enter the light dispersion means 19 at slightly-spaced-apart positions thereon. Consequently, the positions of light rays resulted from the light dispersion are slightly spaced apart from one another even if the light rays have the same wavelengths. However, the determination areas 15a, 15b and 15c have a size sufficiently smaller than the size of each of the light receiving areas 21 arranged in the light receiving device 20 and, further, lights with different wavelengths can be sufficiently separated from one another by spacing the light division means 19 and the light receiving device 20 apart from each other by a sufficient distance. Accordingly, lights with the same wavelength (range) can be received by the same light receiving area 21, even if the lights were completely reflected by different determination areas 15a, 15b and 15c.

Figure 3:
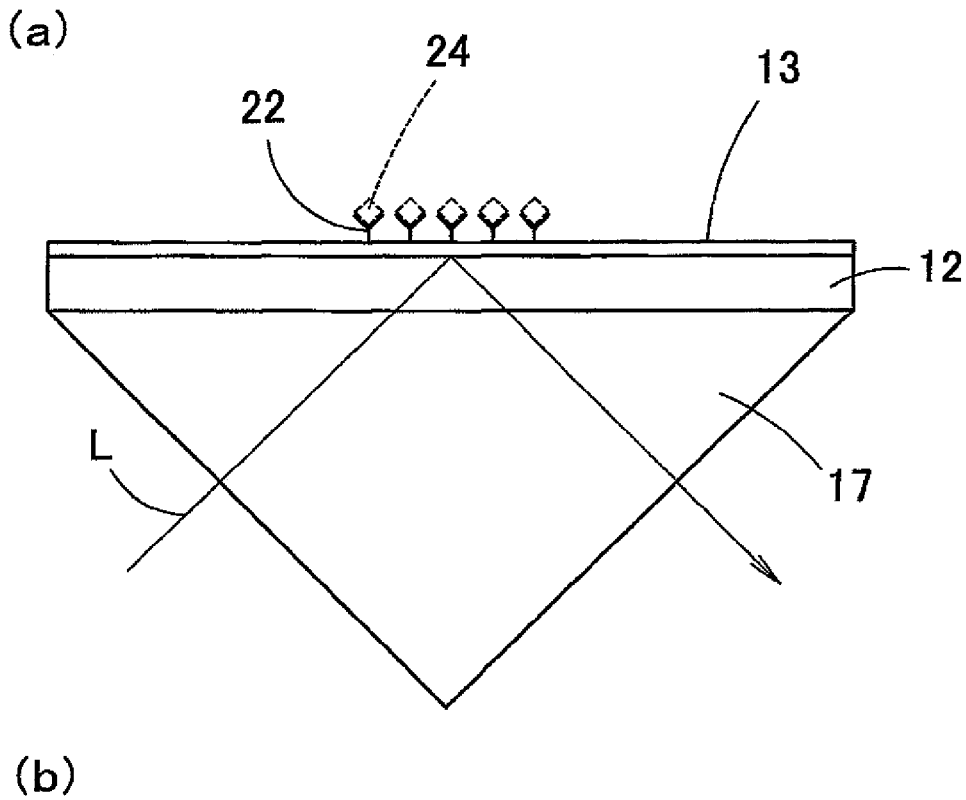
FIG. 3(a) is a view illustrating a surface plasmon resonance sensor having a metal layer and an antibody fixed to the upper surface of the metal layer for forming a determination area.
FIG. 3(b) is a view illustrating a characteristic detected by a light receiving portion therein.
Figure 3:
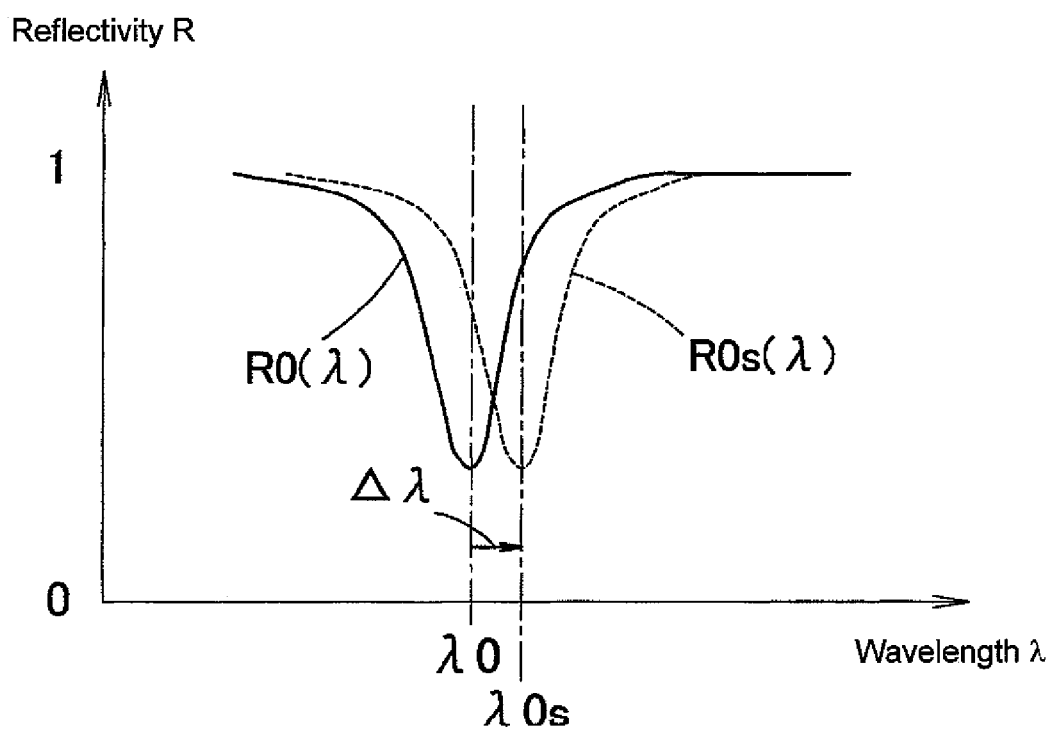

Next, the principle of the measurement by the surface plasmon resonance sensor 11 will be described. FIG. 3(a) illustrates a surface plasmon resonance sensor having a metal layer 13 and an antibody 22 fixed to the upper surface of the metal layer 13 for forming a single determination area. Further, FIG. 3(b) illustrates a spectral characteristic of light L completely reflected by the interface between the transparent substrate 12 and the metal layer 13 in the determination area, when the light L is directed to the determination area of the surface plasmon resonance sensor 11 at such an angle that the light L is completely reflected thereby. In the determination area within which the light L is completely reflected, an evanescent wave having an electric field distribution is generated at the surface of the metal layer 13. Further, if the wave number and the frequency of the evanescent wave are coincident with the wave number and the frequency of surface plasmon, this induces resonance therebetween, which causes optical energy of the incident light to shift to the surface plasmon, thereby reducing the intensity of the reflected light at this wavelength. Accordingly, from determination of a spectral characteristic of the reflected light, it is revealed that the reflectivity is minimized at a certain absorption wavelength $\lambda 0$ (hereinafter, referred to as a characteristic wavelength), as in a characteristic designated by $R0(\lambda)$ in FIG. 3(b).

Next, if the same measurement is performed at a state where an antigen 24 which can specifically combine with the antibody 22 in the determination area has combined therewith, the characteristic is changed to $R0s(\lambda)$ illustrated in FIG. 3(b), and the characteristic wavelength is shifted by $\Delta\lambda$ to $\lambda 0s$. The amount of the shift $\Delta\lambda(=\lambda 0s-\lambda 0)$ is changed with the amount of the antigen 24 specifically combined with the antibody 22. Accordingly, by determining the amount of wavelength shift $\Delta\lambda$ from the spectral characteristic of the reflected light, it is possible to determine whether or not the antigen 24 has combined with the antibody 22 or it is possible to determine the amount of the antigen 24 specifically combined with the antibody 22.

Considering cases where two or more types of antibodies are fixed on the metal layer 13, in this case, different types of antibodies specifically combine with the respective antibodies and, accordingly, it is expected that inspections can be performed on two or more types of antigens at one time. However, in actual, when light reflected at the respective determination areas having different antibodies is received by the single light receiving device 20, the characteristic wavelengths of the lights reflected by the respective determination areas are overlapped with one another, thereby making it impossible to perform determinations.

Figure 4:
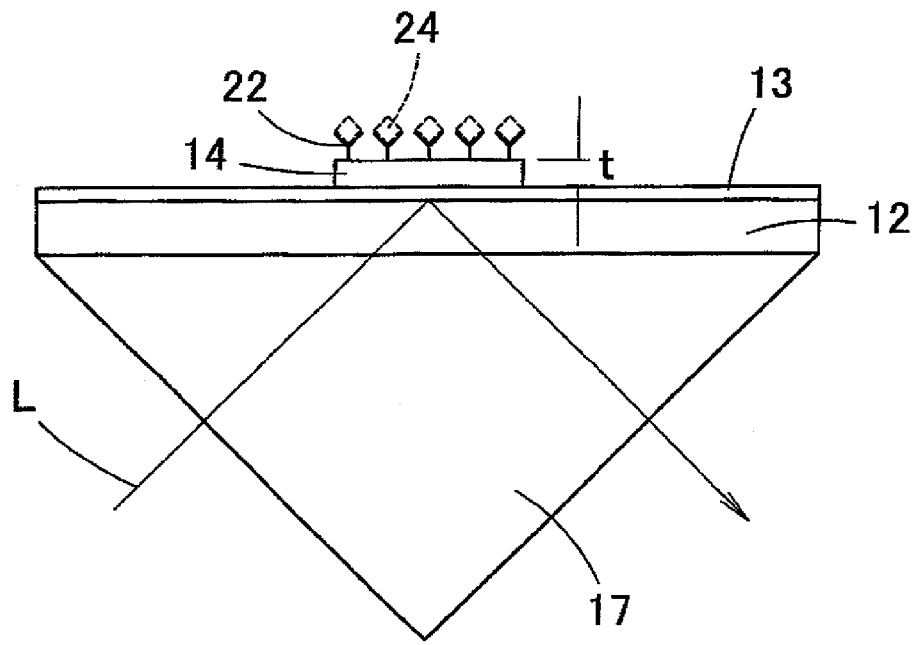
FIG. 4(a) is a view illustrating a surface plasmon resonance sensor having a metal layer and dielectric layers formed on the metal layer.
FIG. 4(b) is a view illustrating a characteristic detected by a light receiving portion therein.
Figure 4:
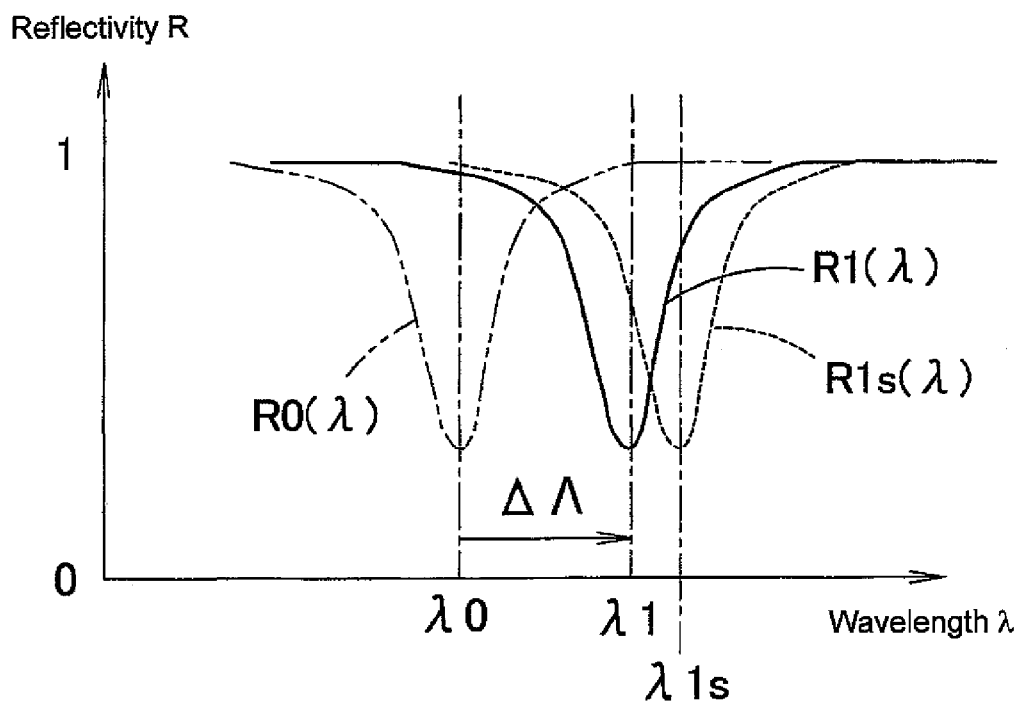

On the other hand, in the case where a dielectric layer 14 having a predetermined thickness t is provided on the metal layer 13 and an antibody 22 is fixed on the dielectric layer 14, as in a surface plasmon resonance sensor illustrated in FIG. 4(*a*), when no antigen has combined with the antibody 22, the characteristic is as a characteristic R1($\lambda$) illustrated in FIG. 4(*b*). Namely, even when no antigen 24 has combined with the antibody 22, the spectral characteristic of the reflected light is changed to the characteristic R1($\lambda$) of FIG. 4(*b*) from the characteristic R0($\lambda$) of when there is provided no dielectric layer 14, and the characteristic wavelength (absorption wavelength) is shifted by $\Delta\Lambda$ to $\lambda 1$. Further, when an antigen 24 has specifically combined with the antibody 22, the characteristic wavelength is as indicated by the characteristic R1s($\lambda$) in FIG. 4(*b*), and the characteristic wavelength is shifted from $\lambda 1$ to $\lambda s$.

Figure 5:
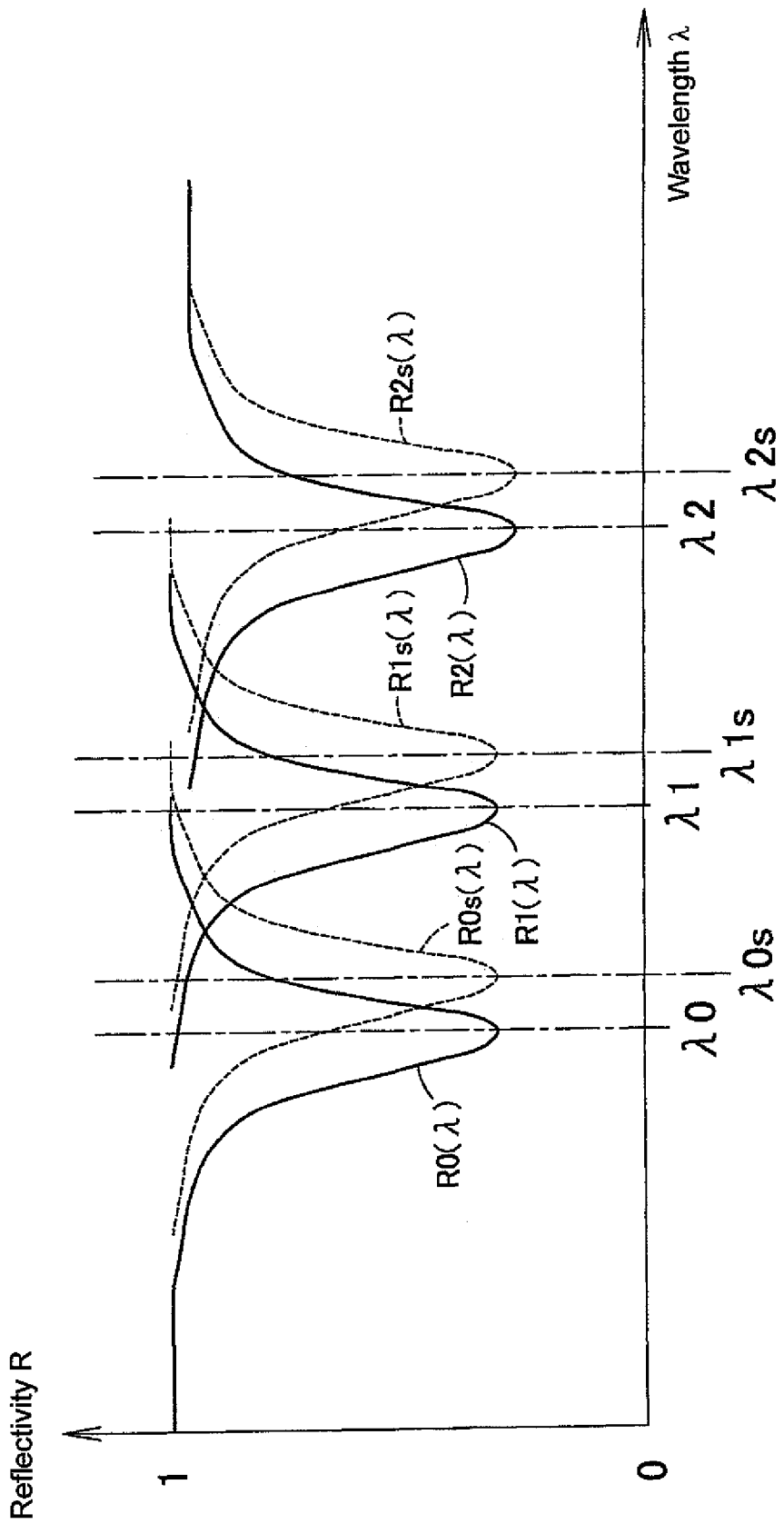
FIG. 5 is a spectral characteristic obtained from a surface plasmon resonance sensor having a plurality of dielectric layers with different thicknesses.

In the surface plasmon resonance sensor 11 according to the first example, the antibodies 22*a*, 22*b* and 22*c* are fixed on the dielectric layers 14*a*, 14*b* and 14*c* having different thicknesses in the respective determination areas 15*a*, 15*b* and 15*c*. Accordingly, as illustrated in FIG. 5, the characteristics R0($\lambda$), R1($\lambda$) and R2($\lambda$) of signals from the respective determination areas 15*a*, 15*b* and 15*c* are shifted by different amounts of wavelength shifts and are separated from one another. This prevents signals from the respective determination areas 15*a*, 15*b* and 15*c* from being mixed with one another, which enables separating the characteristic wavelengths $\lambda 0$, $\lambda 1$ and $\lambda 2$ of the respective signals from one another with higher accuracy.

More specifically, when no antigen has combined, signals from the determination area 15*a* have a characteristic having a characteristic wavelength of $\lambda 0$ as a characteristic R0($\lambda$) of FIG. 5 and, when an antigen which can specifically combine with the antibody 22*a* has combined therewith, signals from the determination area 15*a* have a characteristic having a characteristic wavelength of $\lambda 0s$ as a characteristic R0s($\lambda$) of FIG. 5. Similarly, when no antigen has combined, signals from the determination area 15*b* have a characteristic having a characteristic wavelength of $\lambda 1$ as a characteristic R1($\lambda$) of FIG. 5 and, when an antigen which can specifically combine with the antibody 22*b* has combined therewith, signal from the determination area 15*b* have a characteristic having a characteristic wavelength of $\lambda 1s$ as a characteristic R1s($\lambda$) of FIG. 5. When no antigen has combined, signals from the determination area 15*c* have a characteristic having a characteristic wavelength of $\lambda 2$ as in a characteristic R2($\lambda$) of FIG. 5 and, when an antigen which can specifically combine with the antibody 22*c* has combined therewith, signals from the determination area 15*c* have a characteristic having a characteristic wavelength of $\lambda 2s$ as a characteristic R2s($\lambda$) of FIG. 5.

Accordingly, by adjusting the thicknesses of the dielectric layers 14*b* and 14*c* such that the characteristic wavelengths $\lambda 0$, $\lambda 1$ and $\lambda 2$ are sufficiently spaced apart from one another, it is possible to detect the respective characteristic wavelengths $\lambda 0$, $\lambda 1$ and $\lambda 2$ and the changed characteristic wavelengths $\lambda 0s$, $\lambda 1s$ and $\lambda 2s$ with higher accuracy without causing them to be mixed with one another, thereby enabling detecting the presence or absence of antigens and the amounts of combined antigens in the respective determination areas 15*a*, 15*b* and 15*c*.

Accordingly, with the surface plasmon resonance sensor 11 according to the first example, it is possible to detect, at one time, different antigen-antibody reactions by fixing different antibodies 22*a*, 22*b* and 22*c* to the respective determination areas 15*a*, 15*b* and 15*c*. This enables performing a plurality of inspections at one time. This enables effectively performing a plurality of inspections at one time by arraying determination areas, which enables fabrication of a bulk-type surface plasmon resonance sensor 11 with reduced size and lower cost. Furthermore, the aforementioned surface plasmon resonance sensor 11 eliminates the necessity of using a CCD as a light receiving device, thereby eliminating the necessity of image processing and also reducing the time required for analyses.

However, the spectra characteristics of light L reflected by the respective determination areas 15*a*, 15*b* and 15*c* are detected by the single light receiving device 20, not individually detected as illustrated in FIG. 5. Accordingly, the intervals between characteristic wavelengths should be determined in consideration of this point. In order to realize this, it is necessary to determine the thicknesses of the respective dielectric layers in such a way as to satisfy a condition referred to as independence. Hereinafter, there will be described the concept of independence required for separating the characteristic wavelengths of respective signals from one another.

Figure 6:
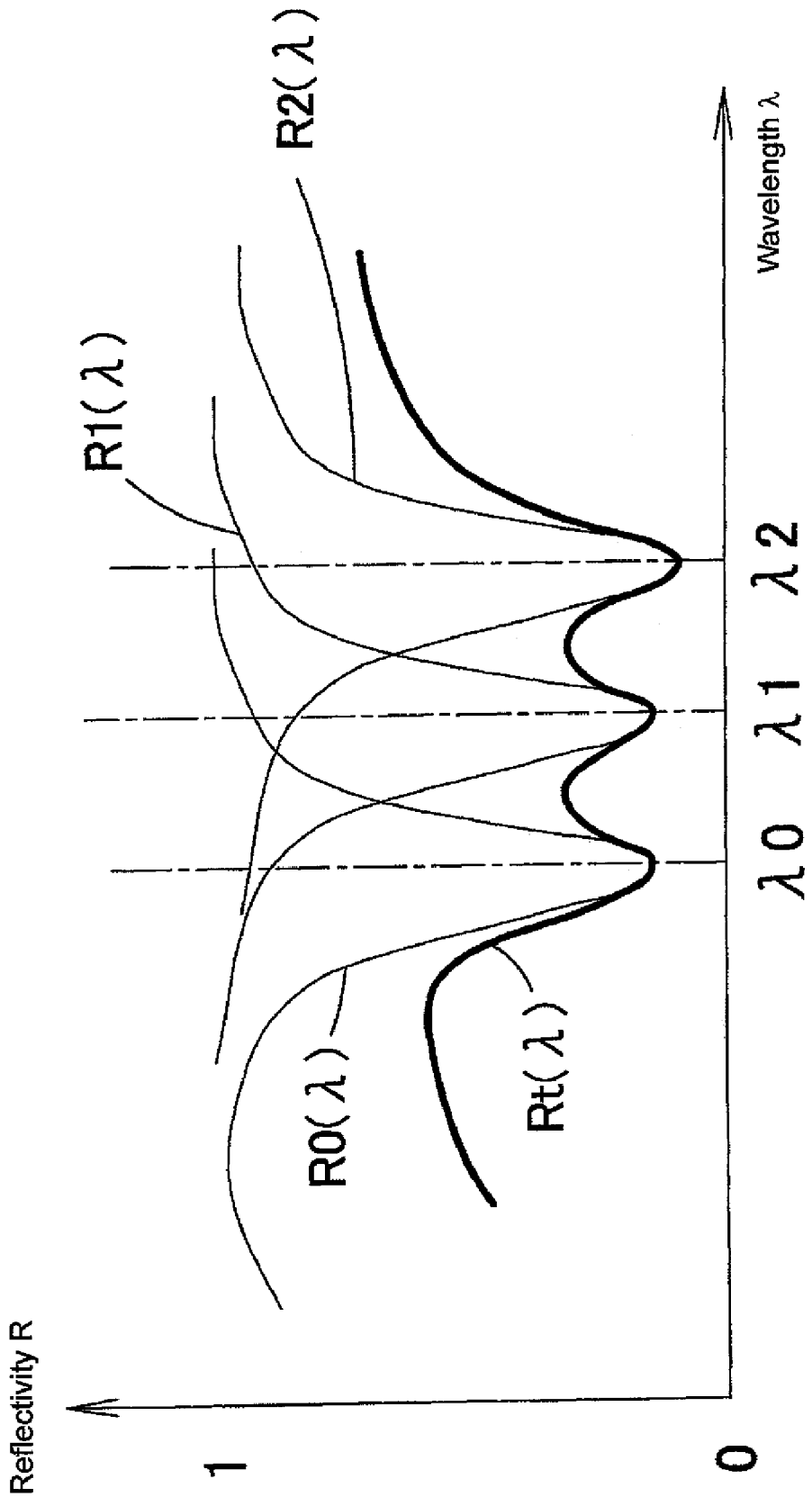
FIG. 6 is a view illustrating the relationship between characteristics R0(λ), R1(λ) and R2(λ) of light completely reflected by respective determination areas and a reflectivity characteristic Rt(λ) detected by a light receiving device.

FIG. 6 illustrates the relationship between the characteristics R0($\lambda$), R1($\lambda$) and R2($\lambda$) of light completely reflected by the determination areas 15*a*, 15*b* and 15*c* and the reflectivity characteristic Rt($\lambda$) detected by the light receiving device 20. The reflectivity characteristic Rt($\lambda$) detected by the light receiving device 20 is the product of the reflectivities of the respective characteristics R0($\lambda$), R1($\lambda$) and R2($\lambda$). Accordingly, the following equation holds.

$$Rt(\lambda)=R0(\lambda)\times R1(\lambda)\times R2(\lambda)$$

If the characteristics of the respective determination areas 15*a*, 15*b* and 15*c* are as R0($\lambda$), R1($\lambda$) and R2($\lambda$) of FIG. 6, the characteristic detected by the light receiving device 20 is as Rt($\lambda$) of FIG. 6.

Figure 7:
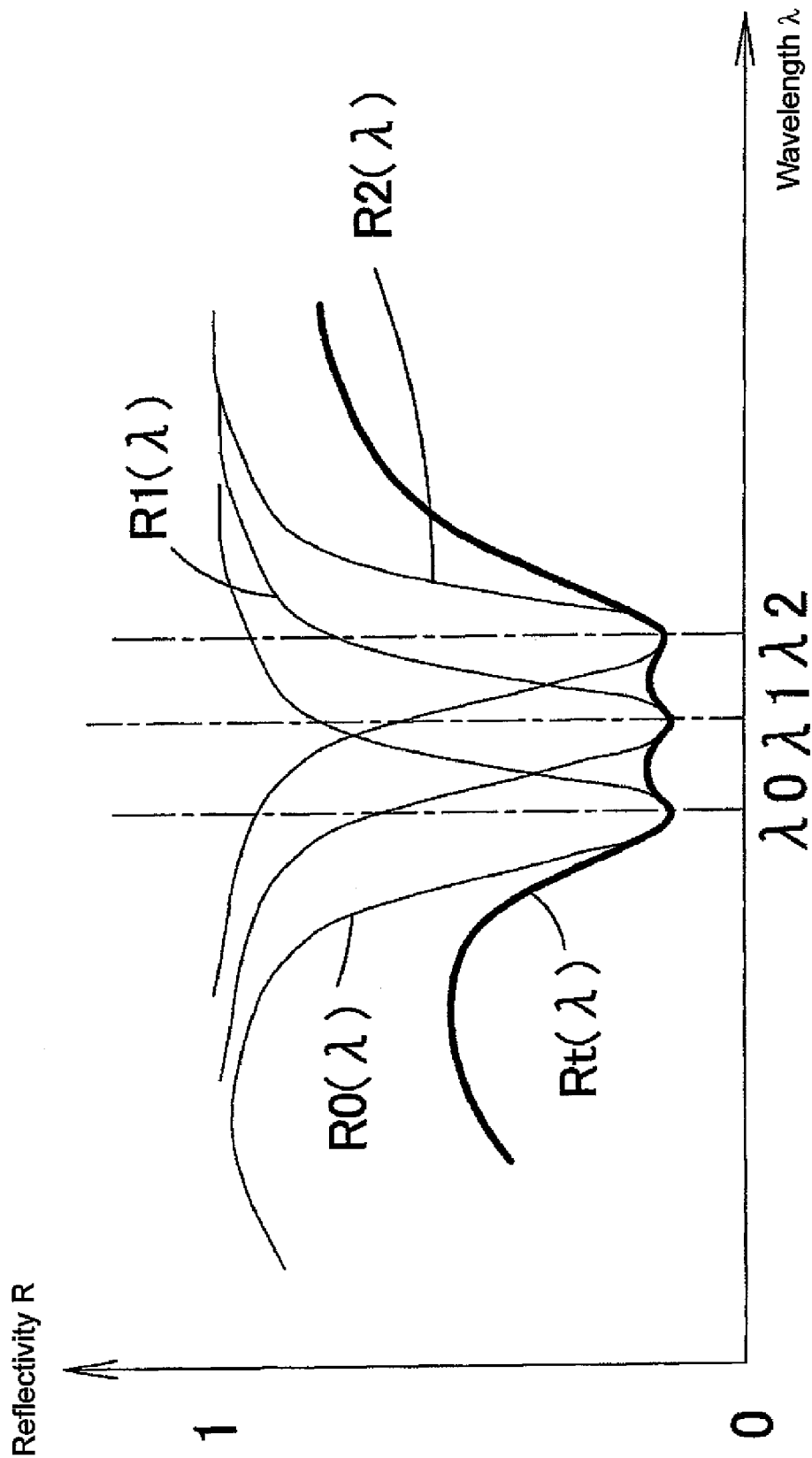
FIG. 7 is a view illustrating the relationship between characteristics R0(λ), R1(λ) and R2(λ) of light completely reflected by respective determination areas and a reflectivity characteristic Rt(λ) detected by a light receiving device, in a case where the independence is poor.

In FIG. 7, it seems that, when comparison is made among the respective characteristics R0($\lambda$), R1($\lambda$) and R2($\lambda$), the respective characteristic wavelengths $\lambda 0$, $\lambda 1$ and $\lambda 2$ are sufficiently separated from one another, but it is difficult to say that the respective characteristic wavelengths $\lambda 1$, $\lambda 1$ and $\lambda 2$ are sufficiently separated from one another when viewing the spectral characteristic Rt($\lambda$) detected actually by the light receiving device 20. Accordingly, in designing the surface plasmon resonance sensor 11, it is necessary to satisfy the condition of independence which will be described generally.

Figure 8:
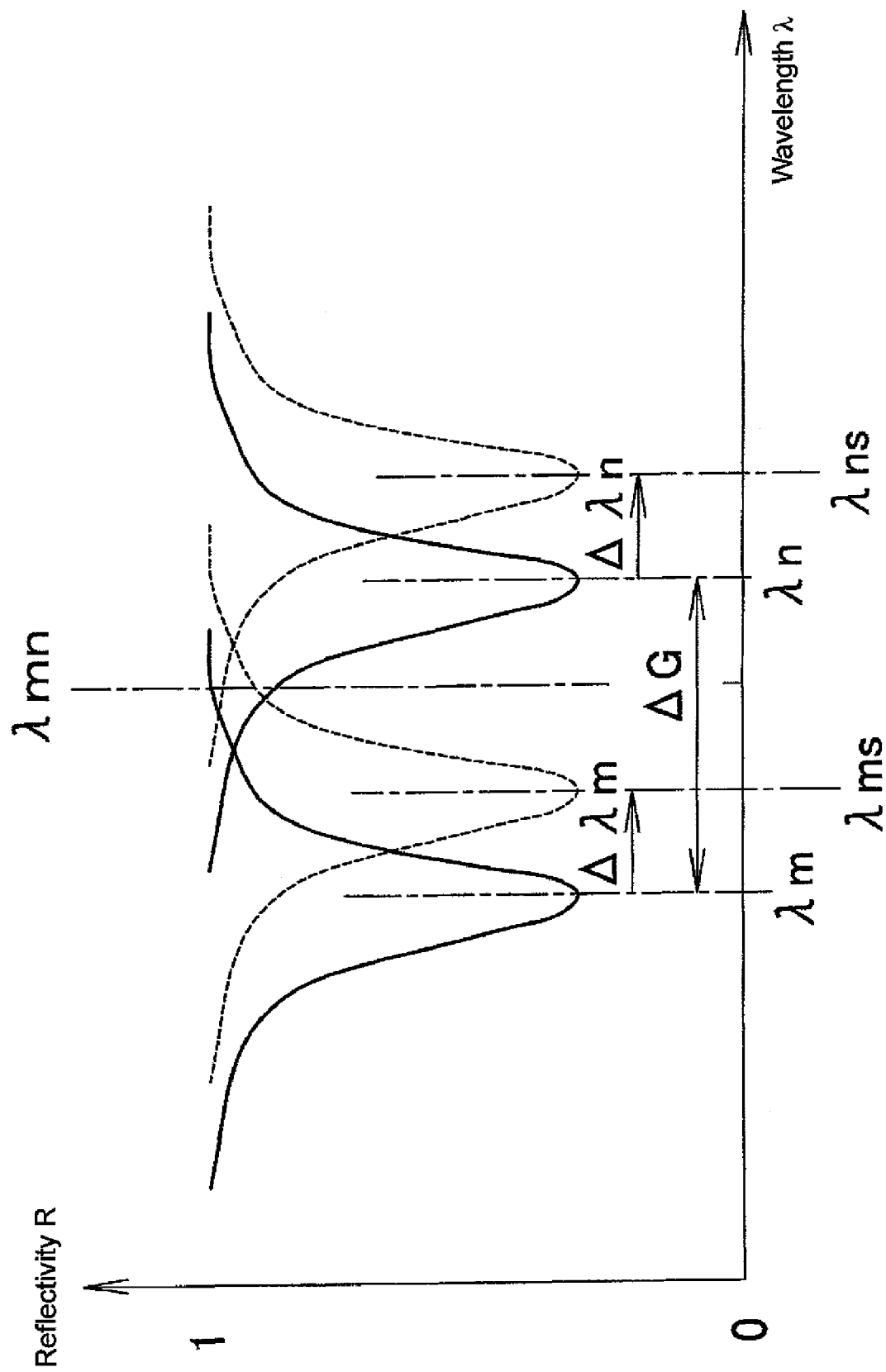
FIG. 8 is a view for explaining independence conditions.

Hereinafter, the characteristic wavelengths will be designated as $\lambda 0$, $\lambda 1$, $\lambda 2$, . . . in the order of shortest to longest. Consideration will be made for the characteristics of light completely reflected by the determination areas having adjacent characteristic wavelengths $\lambda m$ and $\lambda n$ ($\lambda m > \lambda n$; $n=m+1$, wherein m is 0 or a positive integer), as illustrated in FIG. 8. It is assumed that the difference between the adjacent two characteristic wavelengths is $\Delta G=\lambda n-\lambda m$. Further, assuming that the characteristic wavelengths of the respective determination areas when antigens have combined with the respective determination areas are λms and λns, the respective wavelength shifts are expressed as follows.

$$\Delta\lambda m = \lambda ms - \lambda m$$

$$\Delta\lambda n = \lambda ns - \lambda n$$

First, it is necessary that an arbitrary pair of spectral characteristics having adjacent characteristic wavelengths satisfies the following relationship, as a condition required for preventing the adjacent characteristic wavelengths from overlapping with one another after being changed (independence condition 1).

$$\Delta G > \Delta\lambda m \quad \text{(Equation 1)}$$

Next, in order to enable detection with higher accuracy, it is necessary to prevent the signal waveforms of the characteristics detected by the light receiving device 20 from being collapsed. The following function is defined now.

$$Fk(\lambda) = R0(\lambda) \times R0s(\lambda) \times R1(\lambda) \times R1s(\lambda) \times \ldots \times Rk(\lambda) \times Rks(\lambda)$$

$$= llRj(\lambda) \times llRjs(\lambda)$$

(where the products are both for the range of from j=0 to j=k)

In the function, the number of determination areas in the sample detection portion 16 is k+1, the wavelength of light is λ, the reflectivities of the respective determination areas are $R0(\lambda), R1(\lambda), R2(\lambda), \ldots, Rk(\lambda)$, and the reflectivities of the respective determination areas when antigens have specifically combined therewith are $R0s(\lambda), R1s(\lambda), R2s(\lambda), \ldots, Rks(\lambda)$. In this case, $llRj(\lambda)$ is the signal characteristic detected by the light receiving device 20 when no antigen has combined with any of the determination areas, and $llRjs(\lambda)$ is the signal characteristic detected by the light receiving device 20 when antigens have combined with all of the determination areas.

An independence condition 2 is that the gradient of the tangent to the aforementioned function $Fk(\lambda)$ at wavelengths $\lambda mn+\Delta\lambda=\lambda x$ ($\Delta\lambda$ used herein is an arbitrary small value other than 0, and λx indicates the vicinity of the inflection pointλmn) near the center wavelength of the minimum inter-wavelength distance between arbitrary adjacent spectral characteristics $Rm(\lambda)$ and $Rn(\lambda)$ as illustrated in FIG. 8 should not be zero, wherein the aforementioned center wavelength of the minimum inter-wavelength distance is expressed as follows.

$$\lambda mn = (\lambda ms + \lambda n)/2 \quad \text{(Equation 2)}$$

Further, the independence condition 2 can be expressed as follows.

$$|dFk(\lambda x)/d\lambda x| > 0 \quad \text{(Equation 3)}$$

In a simple term, the equation 3 means that the twice differentiation of $Fk(\lambda)$ should not be zero. Further, the larger the value of $[dFk(\lambda x)/d\lambda x]$, the better.

Further, the aforementioned (Equation 2) can be used when its waveform is bilaterally symmetrical and the center wavelength of the minimum inter-wavelength distance is the inflection point, but in other cases (the waveform is not bilaterally symmetrical), the aforementioned (Equation 2) can not be used. In cases where its waveform is not bilaterally symmetrical, the condition is that the twice differentiation should not be zero.

Also, the independency condition 2 is that the minimum value $Ris(\lambda is)$ of an arbitrary spectral characteristic after antigens have adhered should be smaller than the value of $Fk(\lambda)/Ri(\lambda)$ at an arbitrary λmn defined by the aforementioned (Equation 2), and the following relationship should be satisfied.

$$Ris(\lambda is) < Fk(\lambda mn)/Ri(\lambda mn) \quad \text{(Equation 4)}$$

In this case, i is an index indicating the arbitrary spectral characteristic and equals to 0, . . . k, m and n are indexes indicating arbitrary adjacent spectral characteristics, $Ris(\lambda is)$ is the value of the spectral characteristic $Ris(\lambda)$ at a characteristic wavelength λis after antigens have adhered, and $Ri(\lambda)$ is the spectral characteristic corresponding to $Ris(\lambda)$ before antigens combine. In consideration of the positional accuracy of the surface plasmon resonance sensor 11 during fabrication and the divergence of the light emitted from the light projection portion 18, it is desirable that the value of the right side of aforementioned (Equation 4) is greater than the value of the left side by 10% or more.

Accordingly, in determining the thicknesses of the dielectric layers in the respective determination areas, it must be noted that the independence condition of the aforementioned (Equation 1) and at least one of the independence conditions of the aforementioned (Equation 3) and the aforementioned (Equation 4) should be satisfied.

Further, usually, the transparent substrate 12 is made of glass or PMMA, the metal layer 13 is made of Au, and the dielectric layers 14a, 14b and 14c are made of $Ta_2O_5$ or PMMA or polycarbonate. In this case, when normal biomolecules are adhered thereto, the characteristic wavelength of signals is shifted by about 50 nm. Accordingly, by making the spacing ΔG between signal characteristic wavelengths to be equal to or more than 100 nm, it is possible to detect the characteristic wavelengths of signals with higher accuracy.

Further, the light receiving device 20 is required to cover all characteristic wavelengths. Namely, there is a need for a light receiving device 20 having a size and a number of cells which can receive light with wavelengths at least in the range of λ0 to λks with required resolution.

Figure 9:
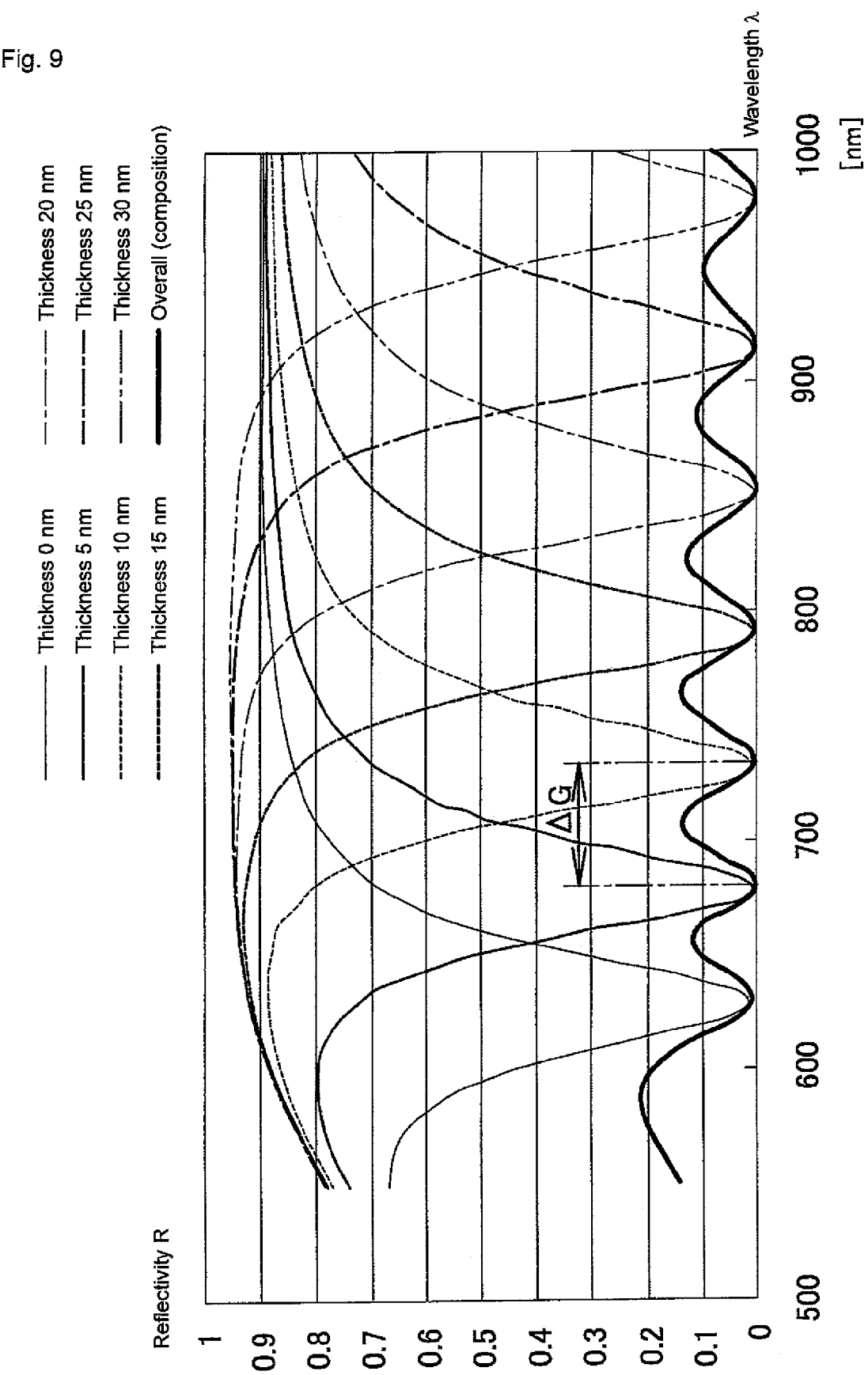
FIG. 9 is a view illustrating the results of simulations.
Figure 10:
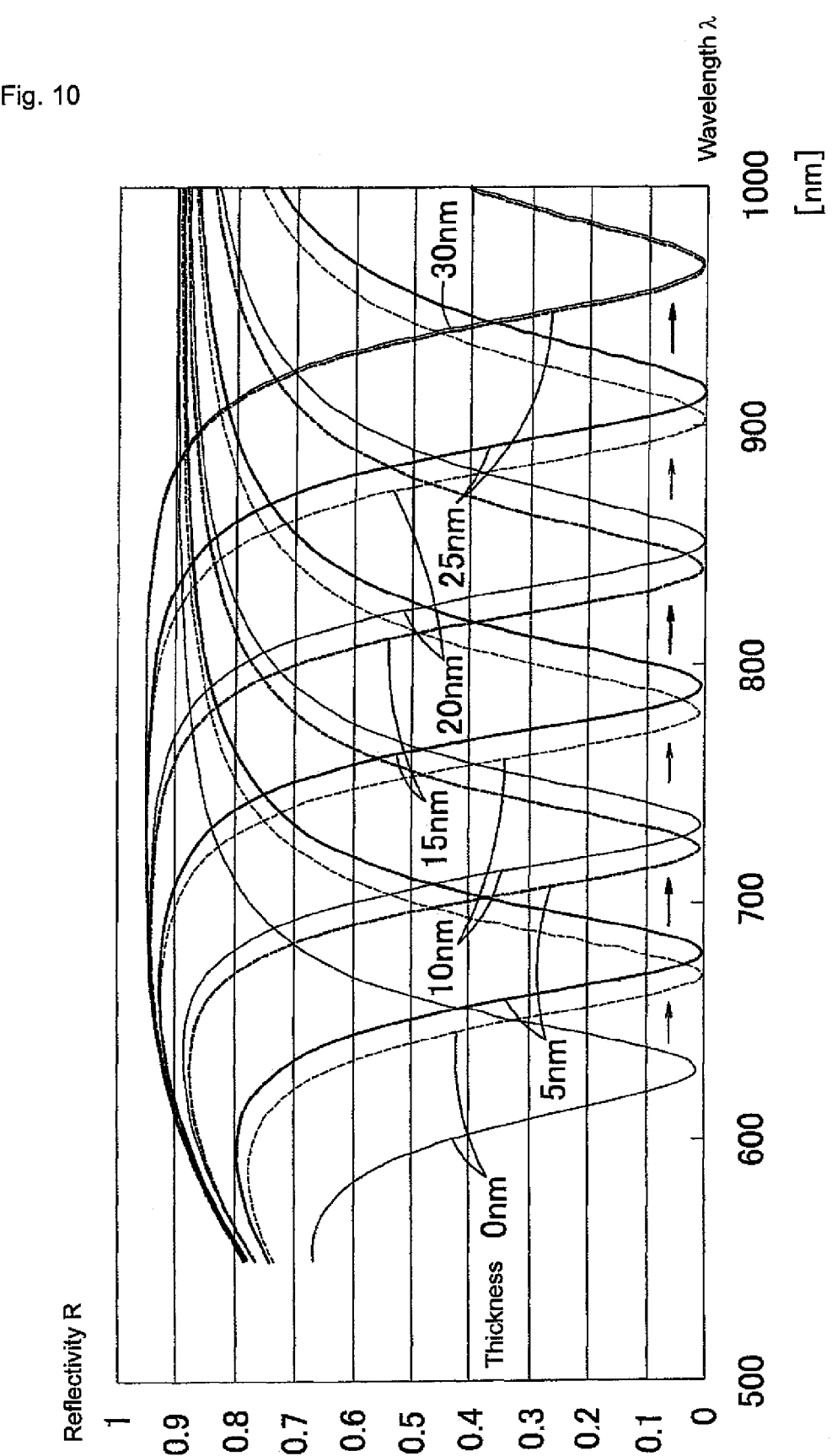
FIG. 10 is a view illustrating the results of simulations.
Figure 11:
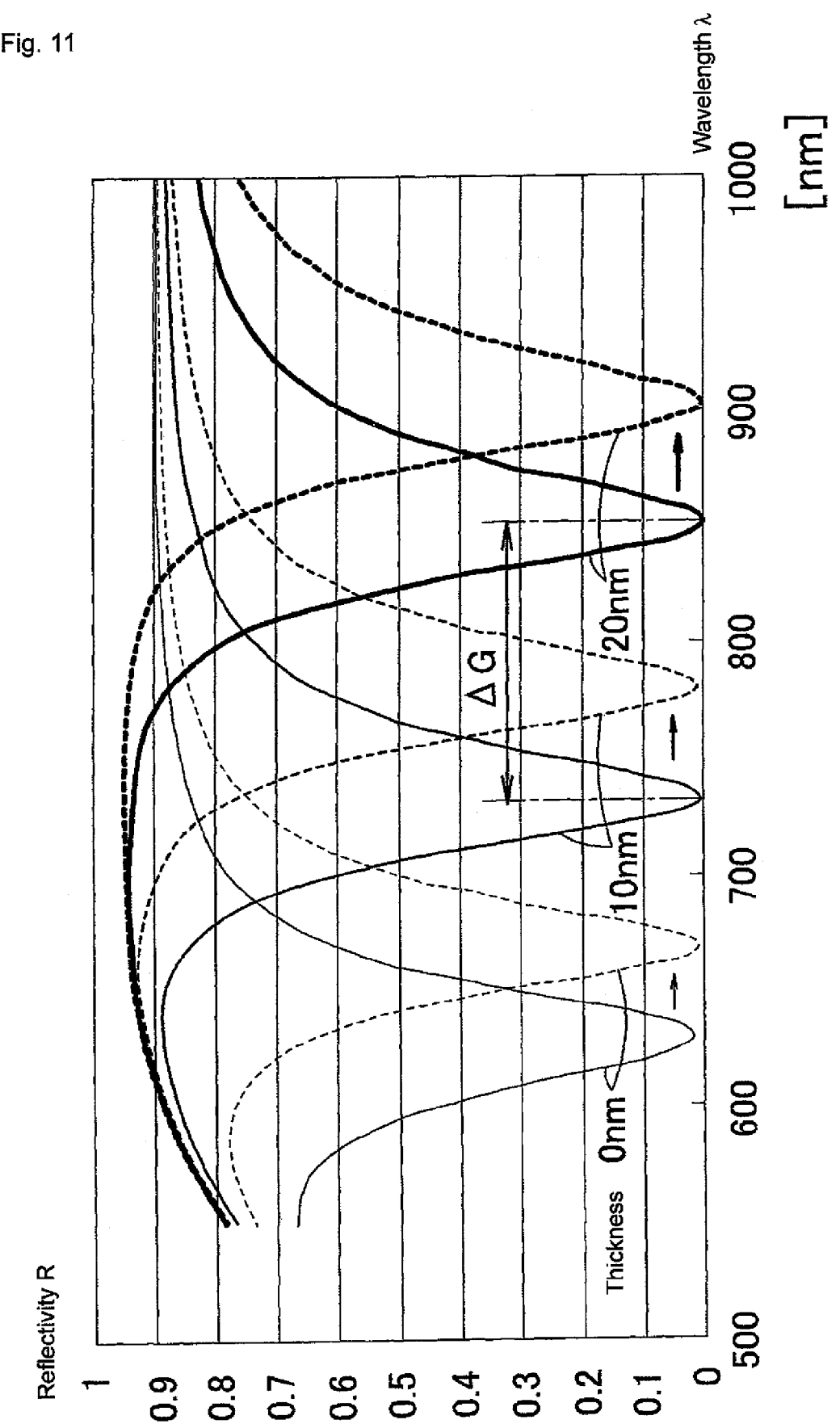
FIG. 11 is a view illustrating the results of simulations.

FIGS. 9, 10 and 11 illustrate the results of simulations. In FIG. 9 and FIG. 10, it was assumed that the transparent substrate was made of PMMA and had a refractive index of 1.492, the metal layer was an Au thin film having a thickness of 50 nm, and the incidence angle of light incident to the metal layer was 75 degree. Further, it was assumed that the number of determination areas was 7, and dielectric layers with thicknesses t of 0 nm (no dielectric layer), 5 nm, 10 nm, 15 nm, 20 nm, 25 nm and 30 nm were formed from $Ti_2O_5$ in the respective determination areas. FIG. 9 illustrates the reflectivity characteristics of the respective determination areas before antigens combine therewith and the overall characteristic detected by the light receiving device at the time. FIG. 10 illustrates the changes of the characteristics from when no antigens have combined with the respective determination areas to when antigens have combined therewith, illustrating, by solid lines, the characteristics before antigens combine while illustrating, by broken lines, the characteristics after antigens combine. In this case, it was temporarily assumed that the size of antigens was 10 nm, and the refractive index of the determination areas after antigens combined therewith was 1.57. In the case where the difference in thickness t between dielectric layers is only 5 nm as described above, the difference ΔG between adjacent characteristic wavelengths before antigens combine is insufficient as illustrated in FIG. 9 and, accordingly, the characteristic wavelength of each characteristic after antigens combine is extremely close, at its longer-wavelength side, to the characteristic wavelength of the adjacent characteristic before antigens combine, which degrades the independence of signals.

On the other hand, FIG. 11 illustrates characteristics of three determination areas having dielectric layers with thicknesses t of 0 nm, 10 nm and 20 nm, illustrating, by solid lines, their characteristics before antigens combines therewith while illustrating, by broken lines, their characteristic after antigens combine therewith. In this case, the difference ΔG between adjacent characteristic wavelengths before antigens combine is sufficient and, accordingly, the characteristic wavelength of each characteristic after antigens combine was sufficiently separated, at its longer-wavelength side, from the characteristic wavelength of the adjacent characteristic before antigens combine.

On the basis of the aforementioned consideration, it is desirable that the thicknesses t of the dielectric layers in the respective determination areas are different from one another by 10 nm or more. In assuming that the light receiving device 20 is capable of detecting wavelengths in the range of 500 nm to 1000 nm, the number of determination areas should be 3 and, accordingly, the thicknesses t of the dielectric layers 14a, 14b and 14c in the respective determination areas 15a, 15b and 15c can be set to 0 nm, 10 nm and 20 nm, respectively.

Figure 12:
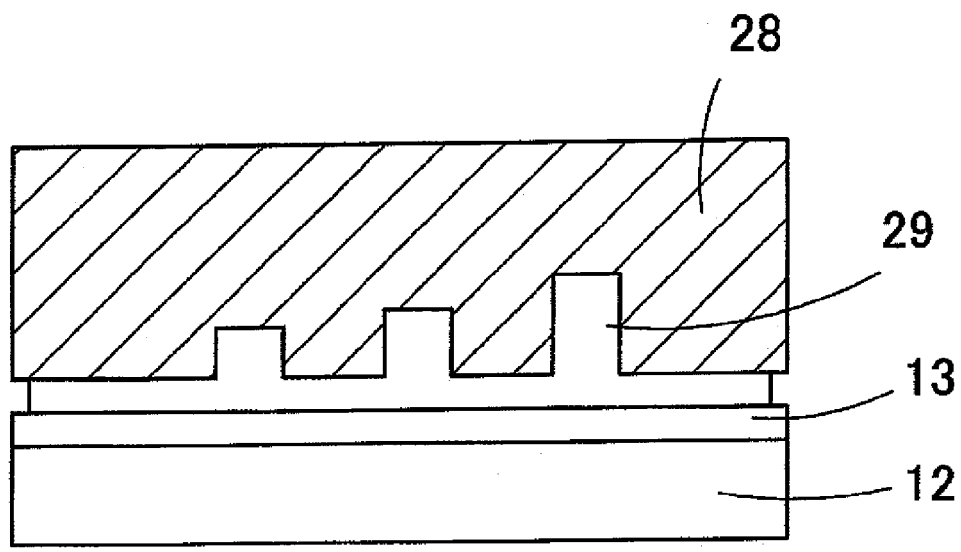
FIG. 12(a), FIG. 12(b), FIG. 12(c) are views illustrating processes for forming dielectric layers with different thicknesses on the upper surface of a metal layer.
Figure 12:
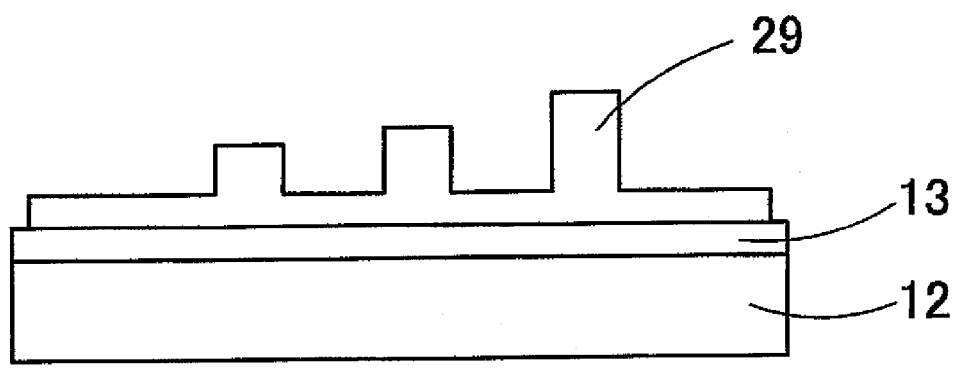
Figure 12:
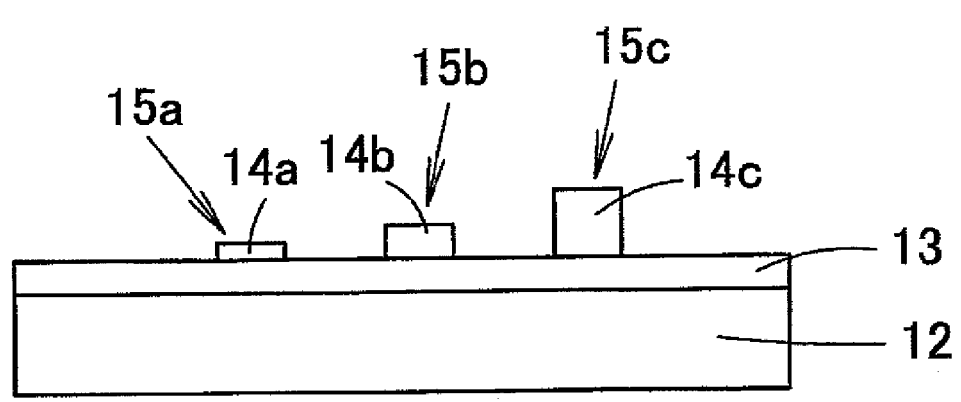

Next, there will be described a method for forming dielectric layers 14a, 14b and 14c with different thicknesses on the upper surface of a metal layer 13. This method is a method for replicating dielectric layers 14a, 14b and 14c using a stamper. The stamper 28 has concave portions having the same shapes as those of the to-be-fabricated dielectric layers 14a, 14b and 14c. In fabricating the dielectric layers 14a, 14b and 14c, a dielectric resin material 29 is preliminarily applied to the upper surface of the metal layer 13 on the transparent substrate 12, then the stamper 28 is pressed against the dielectric resin material 29 from above as illustrated in FIG. 12(a), then the dielectric resin material 29 is shaped by sandwiching the dielectric resin material 29 between the metal layer 13 and the stamper 28. After the dielectric resin material 29 is cured, the stamper 28 is separated therefrom, which causes the dielectric resin material 29 to form the shapes of the dielectric layers 14a, 14b and 14c on the upper surface of the metal layer 13, as illustrated in FIG. 12(b). Next, wet etching or dry etching is applied to the dielectric resin material 29 to eliminate the unnecessary portions of the dielectric resin material 29, which results in completion of the formation of the dielectric layers 14a, 14b and 14c from the dielectric resin material 29, as illustrated in FIG. 12(c).

With the aforementioned method for shaping the dielectric resin material 29 (particularly, an UV-curable resin) using the stamper 28, it is possible to fabricate fine dielectric layers 14a, 14b and 14c with higher accuracy, which enables increasing the density of determination areas or reducing the size of the surface plasmon resonance sensor 11.

SECOND EXAMPLE

Figure 13:
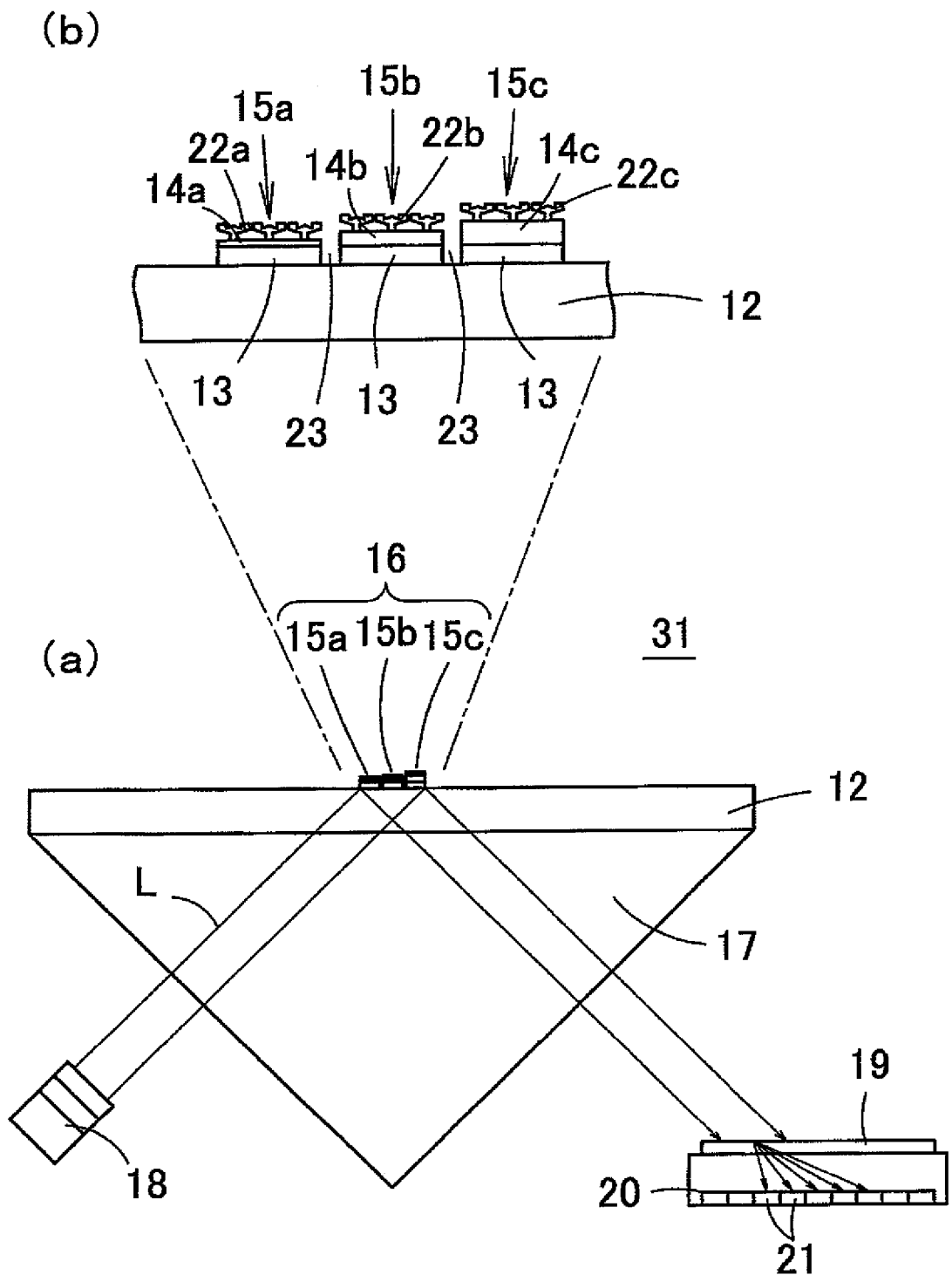
FIG. 13(a) is a schematic view illustrating a surface plasmon resonance sensor according to a second example of the present invention.
FIG. 13(b) is an enlarged view of a sample detection portion therein.

FIG. 13(a) is a schematic view illustrating a surface plasmon resonance sensor 31 according to a second example of the present invention, and FIG. 13(b) is a view illustrating a sample detection portion 16 therein, in an enlarged manner. In the first example, the metal layer 13 is formed in the areas outside of the determination areas 15a, 15b and 15c, but, in the surface plasmon resonance sensor 31 according to the second example, a metal layer 13 is not provided in the areas outside of determination areas 15a, 15b and 15c and is not exposed through the dielectric layers 14a, 14b and 14c. Accordingly, a transparent substrate 12 is exposed at the areas outside of the determination areas 15a, 15b and 15c, which enables applying hydrophilic processing or hydrophobic processing to the areas other than the determination areas 15a, 15b and 15c. This can prevent antigens from adhering to the areas other than the determination areas 15a, 15b and 15c, which can reduce signal noises due to unnecessarily-fixed antigens, thereby increasing the determination accuracy.

Figure 14:
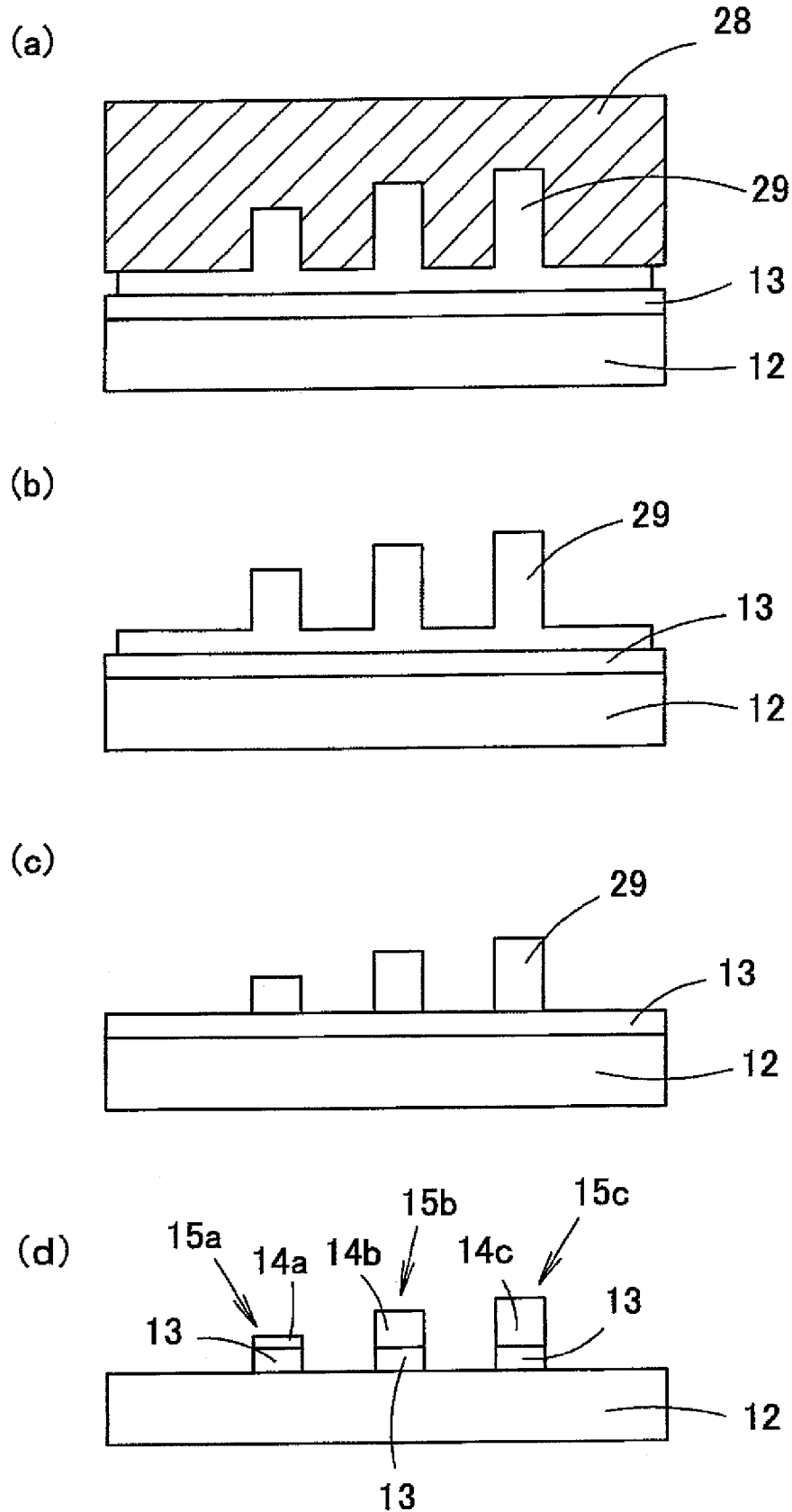
FIGS. 14(a), 14(b) and 14(c) are process views illustrating a method for fabricating determination areas according to the second example.

FIG. 14 is a view illustrating a method for fabricating the determination areas 15a, 15b and 15c according to the second example. FIGS. 14(a) to (c) illustrate the same processes as those of FIGS. 12(a) to (c) in the first example. In the case of the second example, at the final step illustrated in FIG. 14(d), dry etching or wet etching is applied to the metal layer 13 using the patterned dielectric resin material 29 as a mask to remove the portions of the metal layer 13 which are exposed through the dielectric resin material 29 (namely, dielectric layers 14a, 14b and 14c).

THIRD EXAMPLE

Figure 15:
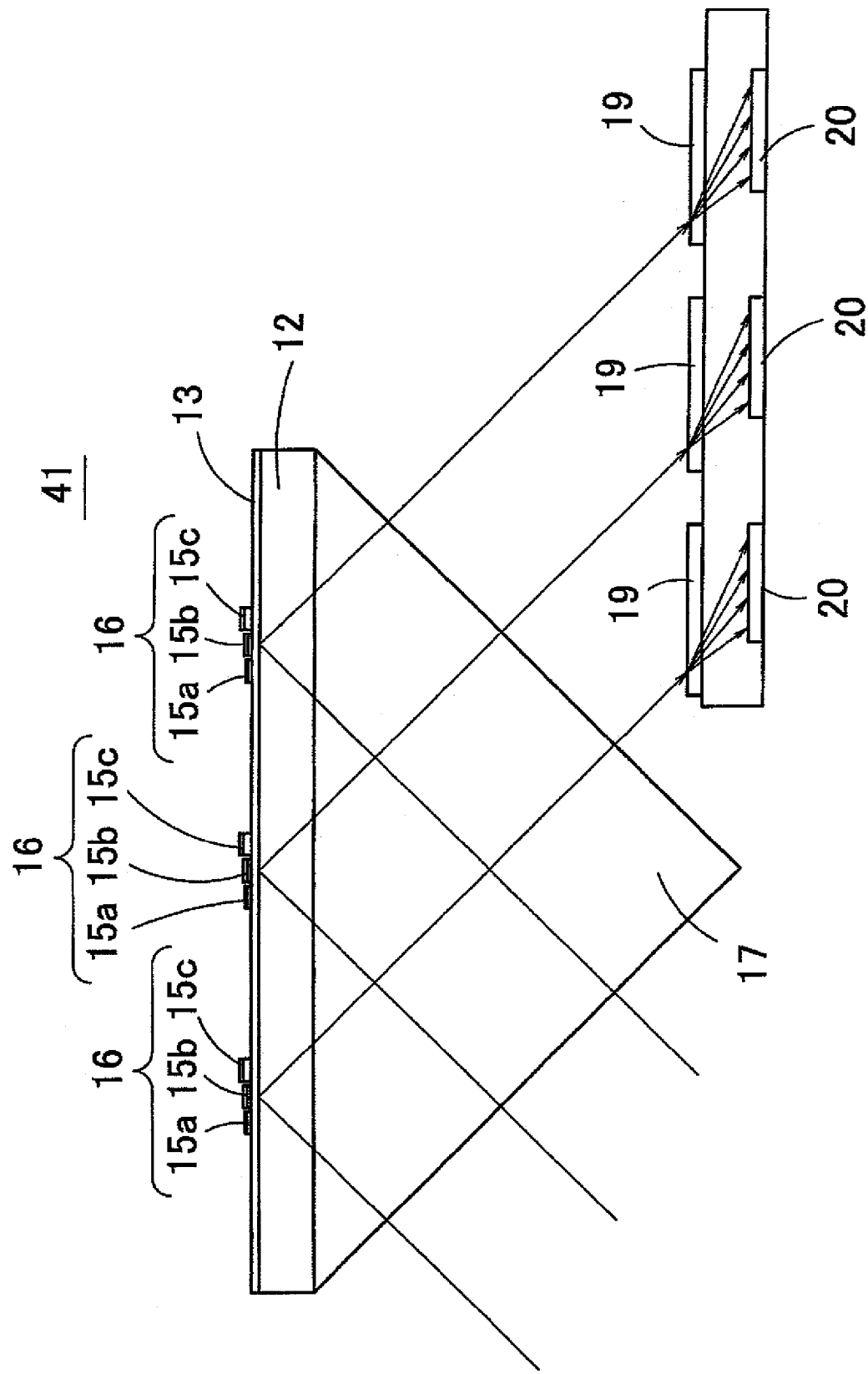
FIG. 15 is a front view illustrating a surface plasmon resonance sensor according to a third example of the present invention.
Figure 16:
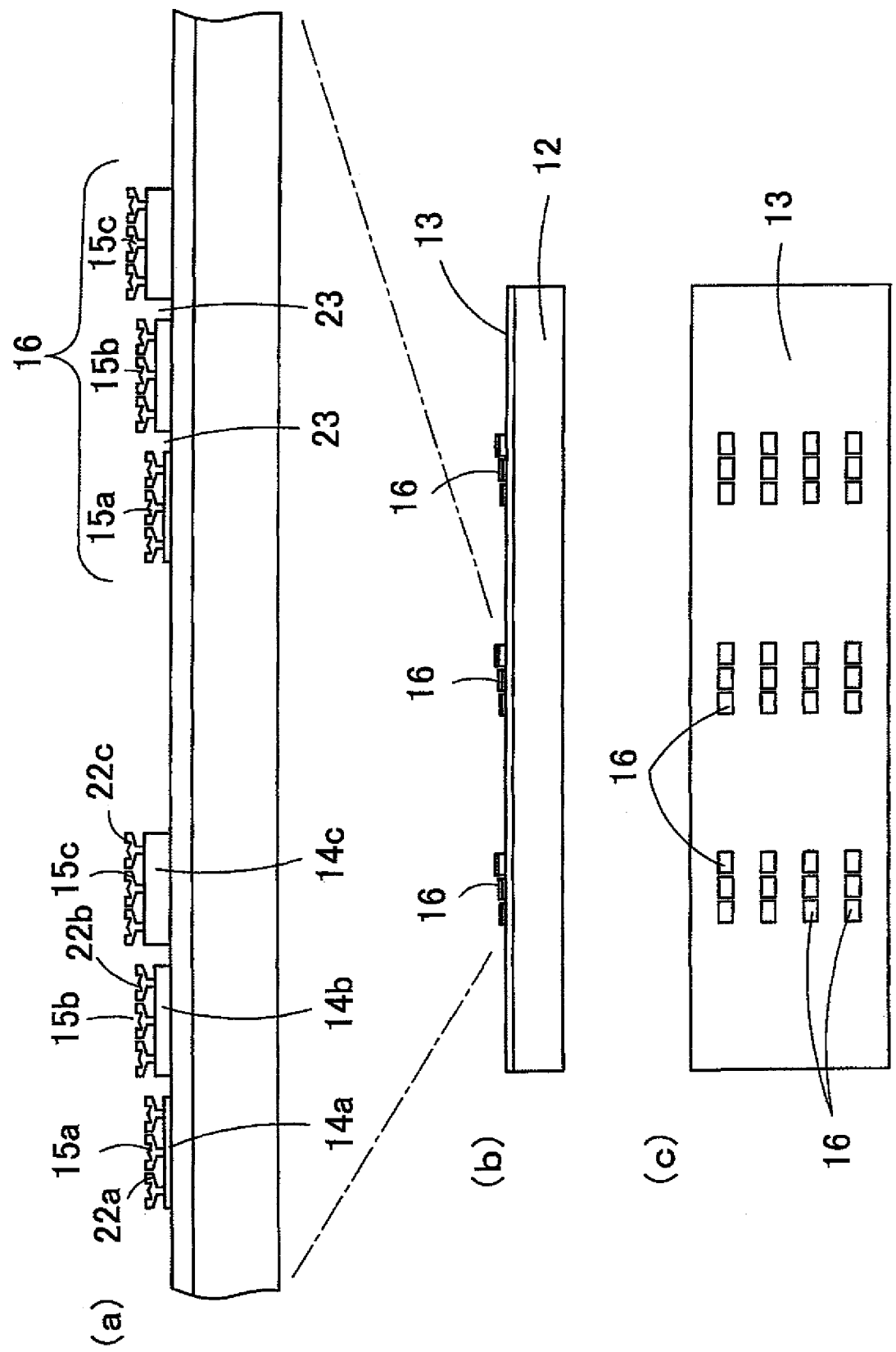
FIG. 16(a) is an enlarged view of sample detection portions in the surface plasmon resonance sensor according to the third example, and FIGS. 16(b) and (c) are a side view and a plan view of the sample detection portions formed on the upper surface of a metal layer.
Figure 17:
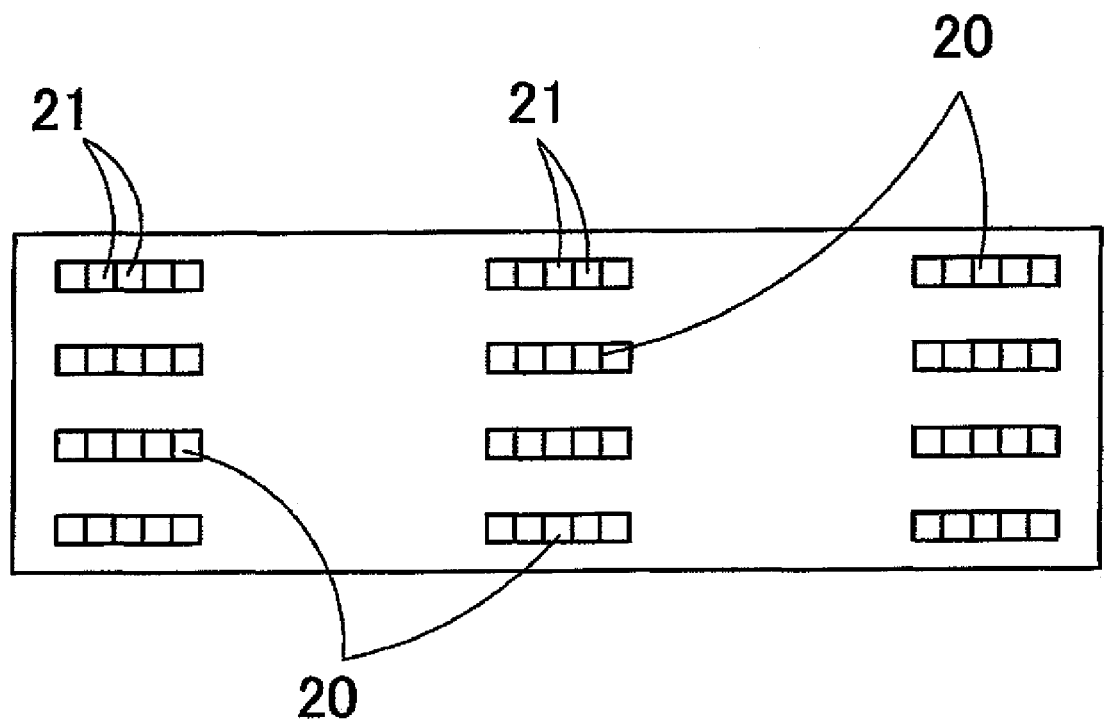
FIG. 17 is a plan view illustrating an array of light receiving devices according to the third example.
Figure 18:
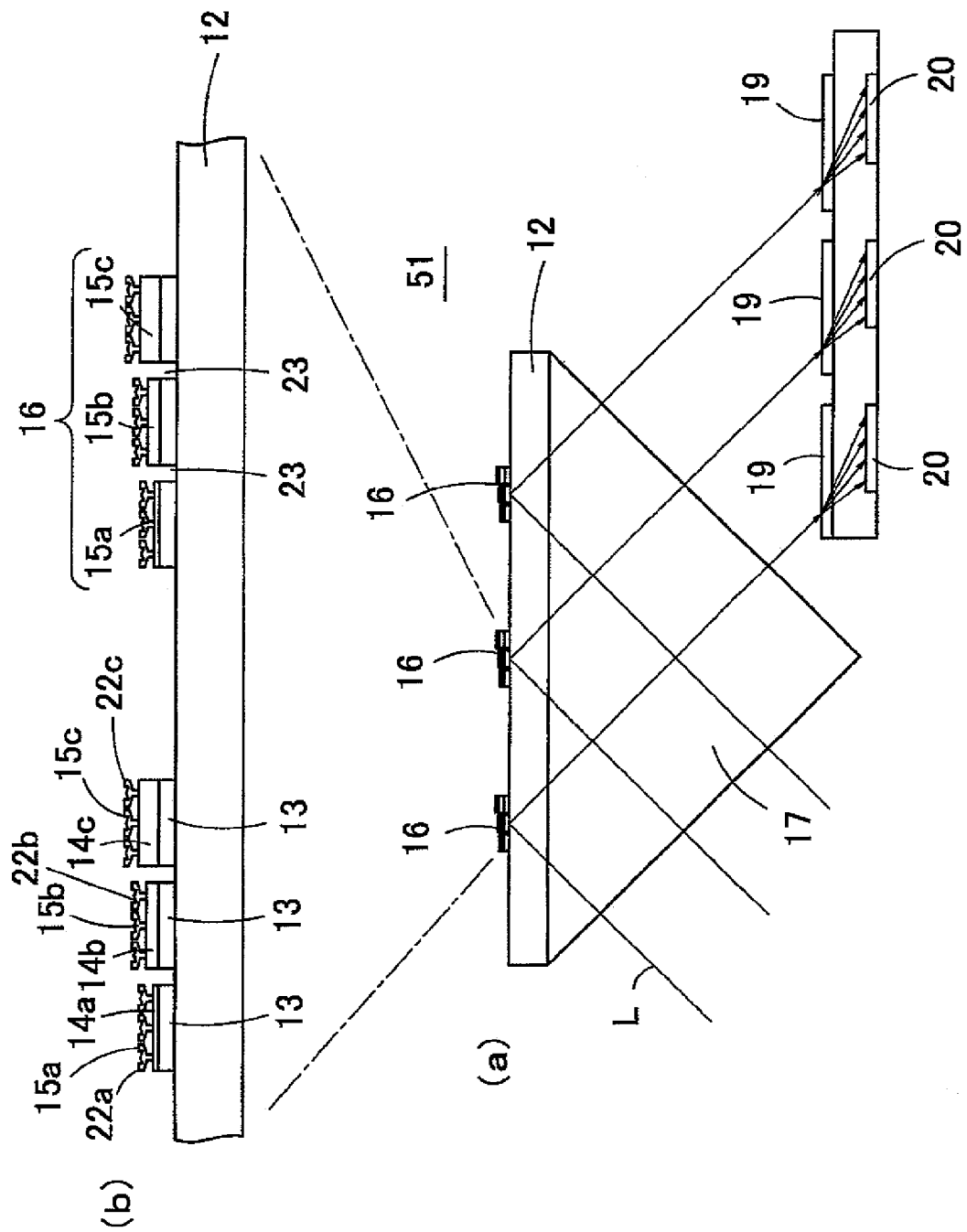
FIG. 18(a) is a front view of a surface plasmon resonance sensor according to a modified example of the third example.
FIG. 18(b) is an enlarged view illustrating sample detection portions therein.

FIG. 15 is a front view illustrating a surface plasmon resonance sensor 41 according to a third example of the present invention. FIG. 16(a) is an enlarged view of sample detection portions 16 in the surface plasmon resonance sensor 41. FIGS. 16(b) and (c) are a side view and a plan view of the sample detection portions 16 formed on the upper surface of a metal layer 13. In the surface plasmon resonance sensor 41 according to the third example, the sample detection portions 16 constituted by a plurality of determination areas 15a, 15b and 15c are arranged longitudinally and laterally (in the illustrated example, three sample detection portions are arranged in the longitudinal direction and four sample detection portions are arranged in the widthwise direction). Further, FIG. 17 is a plan view illustrating an array of light receiving devices 20, illustrating a plurality of light receiving devices 20 arranged longitudinally and laterally such that they correspond to the respective sample detection portions 16.

Thus, as illustrated in FIG. 15, spectral characteristics of light L reflected by the respective sample detection portions 16 are individually detected by the respective light receiving devices 20, which enables the surface plasmon resonance sensor 41 according to the third example to perform an extremely greater number of inspections (36(=3×12) types of inspections, in the illustrated example) at one time, thereby significantly increasing the inspection efficiency. However, the numbers of sample detection portions 16 arranged longitudinally and laterally and the way of arrangement are not limited to those illustrated in the figure.

Further, in the example, similarly, the metal layer 13 can be removed at the areas other than the determination areas 15a, 15b and 15c, in order to prevent the metal layer 13 from being exposed through the dielectric layers 14a, 14b and 14c, which enables applying hydrophilic processing or hydrophobic processing to the areas other than the determination areas 15a, 15b and 15c for preventing adhesion of antigens thereto.

FOURTH EXAMPLE

Figure 19:
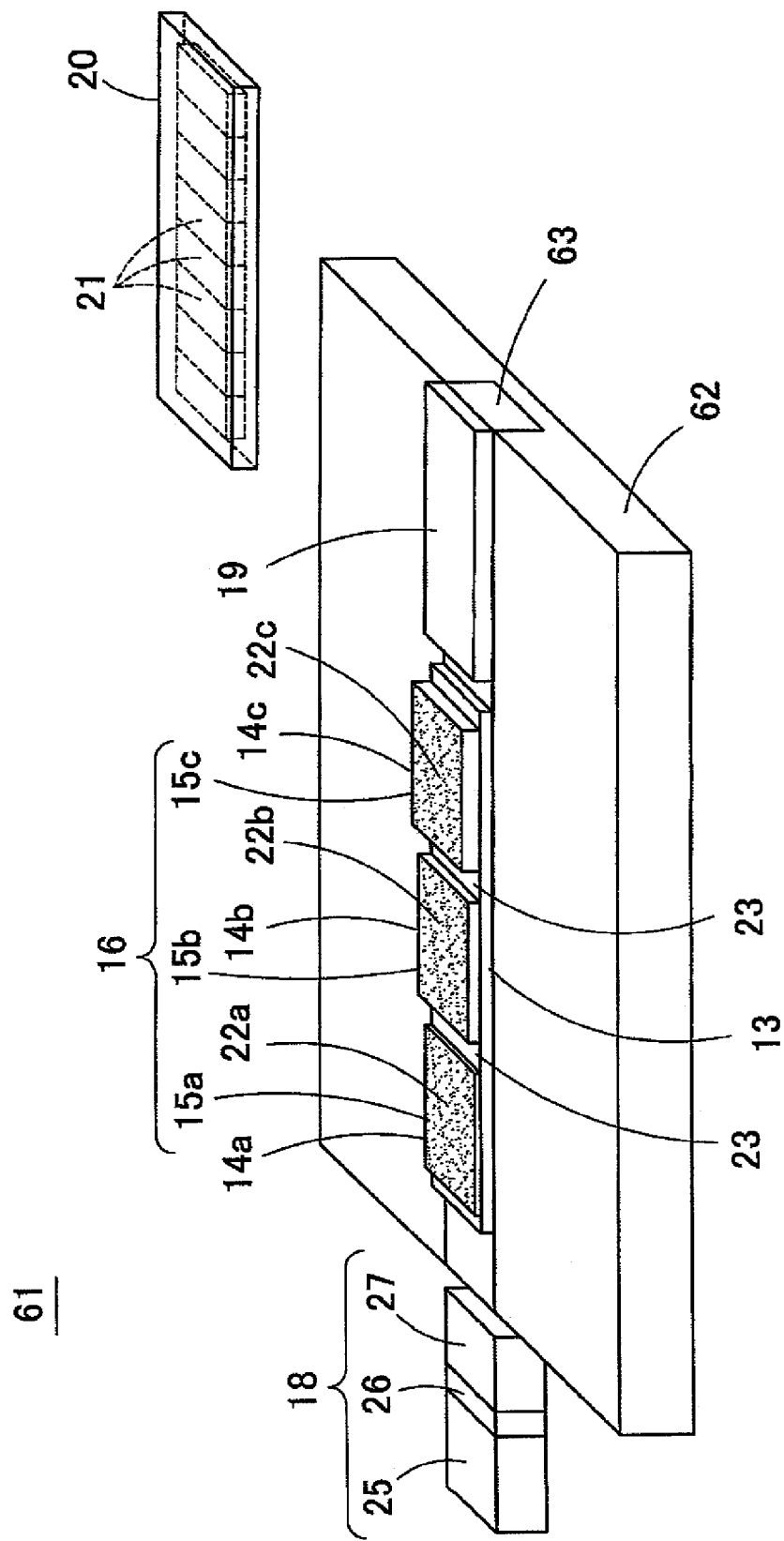
FIG. 19 is a perspective view illustrating a surface plasmon resonance sensor according to a fourth example of the present invention.
Figure 20:
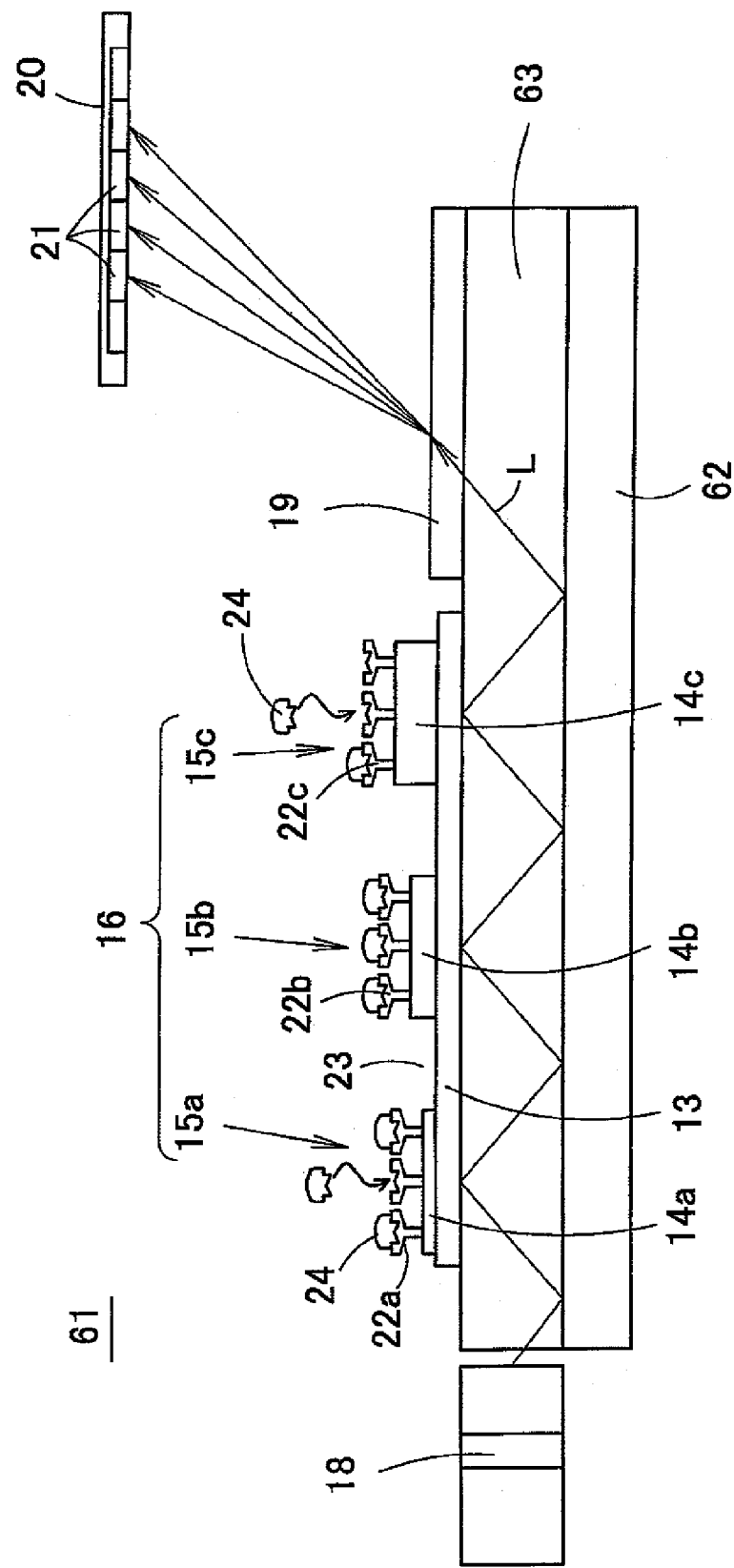
FIG. 20 is a side view of the surface plasmon resonance sensor according to the fourth example of the present invention.

FIG. 19 is a perspective view illustrating a surface plasmon resonance sensor 61 according to a fourth example, and FIG. 20 is a side view of the same. The surface plasmon resonance sensor 61 according to the fourth example is an optical-waveguide-type surface plasmon resonance sensor using a multi-mode type optical waveguide.

The surface plasmon resonance sensor 61 includes a clad 62 made of a transparent plastic and having a slot, and a single core 63 made of a transparent plastic having a refractive index greater than that of the clad 62. A metal layer 13 (metal thin film) is formed on the upper surface of the core 63. The metal layer 13 is made of Au, Ag, Cu and the like formed on the upper surface of the core 63 by vacuum deposition or sputtering.

On the upper surface of the metal layer 13, there is formed a sample detection portion 16 constituted by a plurality of determination areas 15a, 15b, 15c. The determination areas 15a, 15b and 15c constituting the sample detection portion 16 are arranged in a line and are spaced apart from one another by an interval 23. In the determination area 15a, a dielectric layer 14a is formed on the upper surface of the metal layer 13, and an antibody 22a is fixed on the dielectric layer 14a. In the determination area 15b, a dielectric layer 14b having a thickness different from that of the dielectric layer 14a is formed on the upper surface of the metal layer 13, and an antibody 22b different from that in the determination area 15a is fixed on the dielectric layer 14b. Further, in the determination area 15c, a dielectric layer 14c having a thickness different from those of the dielectric layers 14a and 14b is formed on the upper surface of the metal layer 13, and an antibody 22c different from those in the determination areas 15a and 15b is fixed on the dielectric layer 14c. Further, in the figure, there are illustrated the three determination areas 15a, 15b and 15c, but the number of determination areas can be 2 or 4 or more. Further, it is necessary only that the dielectric layers 14a, 14b and 14c have different thicknesses and, also, any of the dielectric layers (for example, the dielectric layer 14a) can have a thickness of 0 (namely, no dielectric layer can be provided). These dielectric layers 14a, 14b and 14c are made of a material with a high dielectric constant such as $Ta_2O_5$ or $TiO_2$ or a dielectric resin material having a high refractive index such as PMMA or polycarbonate.

The areas of the dielectric layers 14a, 14b and 14c (any of the determination areas can have no dielectric layer) formed on the metal layer 13 form the respective determination area 15a, 15b and 15c, and the determination areas 15a, 15b and 15c including the dielectric layers having different thicknesses (including a thickness of 0) collectively form the single sample detection portion 16.

Near one of the end surfaces of the core 63, there is placed a light projection portion 18 such as a white light source for emitting white light and a multi-wavelength light source for emitting light in a plurality of predetermined wavelength ranges. The light projection portion 18 includes a light source 25 such as a light emitting diode (LED), a semiconductor laser device (LD) or a halogen lamp, a polarizer 26 which converts light emitted from the light source 25 into linear polarized light in the direction parallel or perpendicular to the metal layer 13, and a collimate optical system 27 for collimating the light emitted from the light projection portion 18 and emitting the collimated light at a predetermined angle. Further, near the other end surface of the core 63, there is installed a light dispersion means 19 so as to be intimately contact therewith and, thereabove, there is placed a light receiving device 20. It is desirable that the light dispersion means 19 is made of a material having a refractive index substantially equal to that of the core 63 or the same material as that of the core 63. By doing this, the light L enters the light dispersion means 19 without being completely reflected by the interface between the upper surface of the core 63 and the light dispersion means 19.

Figure 21:
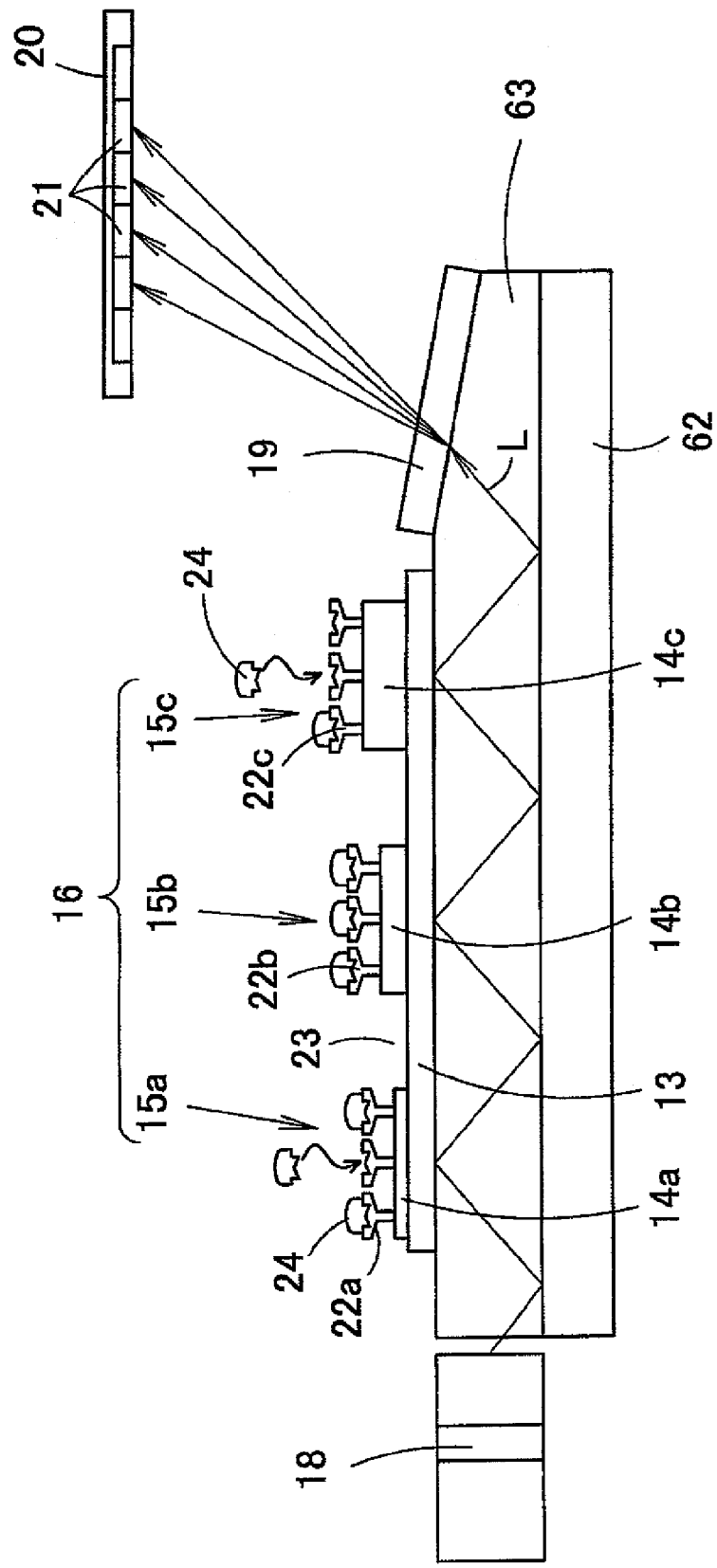
FIG. 21 is a side view of a surface plasmon resonance sensor, for explaining a method for preventing the complete reflection of light by the interface of a light dispersion means installed on the upper surface of an end portion of a core.

Further, as a method for preventing complete reflection of the light L at the interface of the light dispersion means 19, the upper surface of the core 63 on which the light dispersion means 19 is installed can be inclined, as illustrated in FIG. 21. The upper surface of the core 63 can be inclined in such an orientation as to reduce the incidence angle of the light L incident to the interface of the light dispersion means 19. By doing this, the light L propagated through the core 63 enters the light dispersion means 19 without being completely reflected thereby. Further, the aforementioned method can be applied to an optical-waveguide-type surface plasmon resonance sensor according to an alternative example which will be described later, as well as to the first example.

The light dispersion means 19 disperses the light which has been completely reflected by the interface between the transparent substrate 12 and the metal layer 13 and then propagated thereto and is constituted by a diffraction grating. The light receiving device 20 includes a plurality of light receiving areas 21 (light receiving cells) which receive dispersed light with different wavelengths and is constituted by a one-dimensional photodiode array or the like.

Thus, in the surface plasmon resonance sensor 61, the light L (polarized light) emitted from the light projection portion 18 enters the core 63 at its one end surface, then propagates through the core 63 while being completely reflected by the inside thereof and diagonally enters the sample detection portion 16. Then, the light L is completely reflected by the interface between the metal layer 13 and the core 63 in the sample detection portion 16, then propagates through the core 63 and reaches the upper surface of the end portion of the core 63 and then is emitted to the outside from the light dispersion means 19. The light passed through the light dispersion means 19 is dispersed into light with different wavelengths by the light dispersion means 19. The lights with respective wavelengths resulted from the light dispersion by the light dispersion means 19 are emitted in different directions and are received by the light receiving device 20. The light receiving areas 21 in the light receiving device 20 are arranged in the direction of the light dispersion by the light dispersion means 19, and the respective light receiving areas 21 receive light with different wavelengths. This enables determining spectral characteristics of the light reflected by the sample detection portion 16 from the amounts of light received by the respective light receiving areas 21.

Further, the determination areas 15a, 15b and 15c are placed such that they are spaced apart from one another by a constant distance, which causes the lights completely reflected by the respective determination areas 15a, 15b and 15c to enter the light dispersion means 19 at slightly-spaced-apart positions thereon. Consequently, the positions of light rays resulted from the light dispersion are slightly spaced apart from one another even if the light rays have the same wavelengths. However, the determination areas 15a, 15b and 15c have a size sufficiently smaller than the size of each of the light receiving areas 21 arranged in the light receiving device 20 and, further, lights with different wavelengths can be sufficiently separated from one another by spacing the light division means 19 and the light receiving device 20 apart from each other by a sufficient distance. Accordingly, lights with the same wavelength (range) can be received by the same light receiving area 21, even if the lights were completely reflected by different determination areas 15a, 15b and 15c.

The principle of measurement by the surface plasmon resonance sensor 61 according to the fourth example is the same as that described with respect to the block-type surface plasmon resonance sensor 11 according to the first example and will not be described in detail. In the surface plasmon resonance sensor 61 according to the fourth example, the antibodies 22a, 22b and 22c are fixed on the dielectric layers 14a, 14b and 14c having different thicknesses in the respective determination areas 15a, 15b and 15c. Accordingly, the characteristic wavelengths of signals from the respective determination areas 15a, 15b and 15c are shifted by different amounts of wavelength shifts and are separated from one another. Further, signals from the respective determination areas 15a, 15b and 15c are prevented from mixing with one another, which can separate the characteristic wavelengths λ0, λ1 and λ2 of the respective signals from one another with higher accuracy, thereby enabling performing a plurality of inspections at one time. This enables effectively performing a plurality of inspections at one time by arraying determination areas, which enables fabrication of a bulk-type surface plasmon resonance sensor 61 with reduced size and lower cost. Furthermore, the aforementioned surface plasmon resonance sensor 61 eliminates the necessity of using a CCD as a light receiving device, thereby eliminating the necessity of image processing and also reducing the time required for analyses.

However, it is desirable that the surface plasmon resonance sensor 61 according to the fourth example satisfies the independence conditions described in the first example, similarly to the surface plasmon resonance sensor 11 according to the first example. Accordingly, in the case of the fourth example, the respective dielectric layers 14a, 14b and 14c have thicknesses different from one another by 10 nm or more. Accordingly, in assuming that the light receiving device 20 is capable of detecting wavelengths in the range of 500 nm to 1000 nm, similarly to that described with respect to the block-type surface plasmon resonance sensor, the number of determination areas should be 3 and, accordingly, the thicknesses t of the dielectric layers 14a, 14b and 14c in the respective determination areas 15a, 15b and 15c can be set to 0 nm, 10 nm and 20 nm, respectively.

Figure 22:
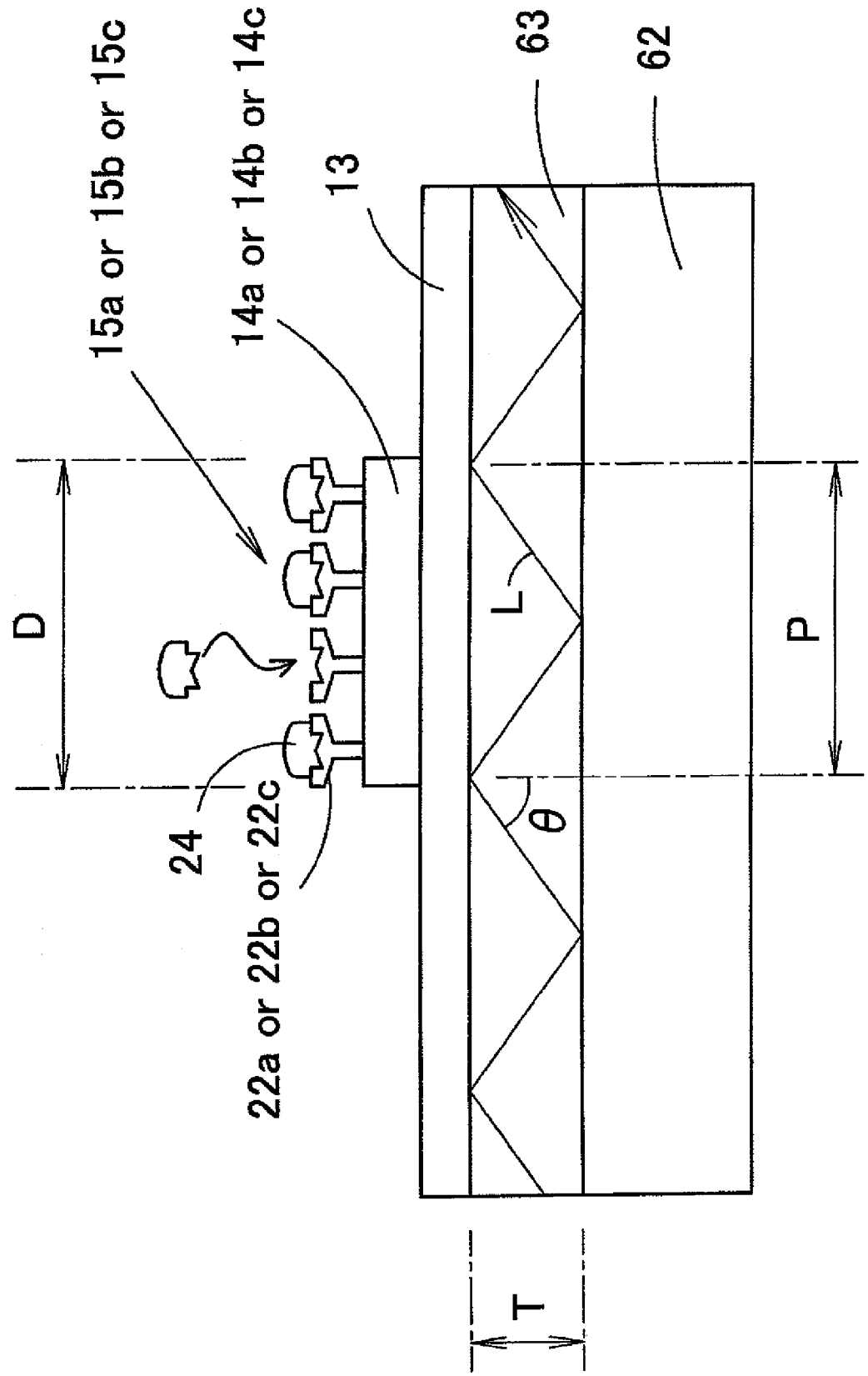
FIG. 22 is a view for explaining conditions for determining the length D of determination areas.

Further, in the case of the optical-waveguide-type surface plasmon resonance sensor 61, in order to provide signals with preferable sensitivity, it is necessary that all the total luminous flux of light propagated through the core 63 are directed to the individual determination areas 15a, 15b and 15c. In order to realize this, the length D of the determination areas 15a, 15b and 15c illustrated in FIG. 22 should be greater than the period P of the light L propagated through the core 63. The period P of light L propagated through the core 63 is expressed as follows, as can be seen from FIG. 22, wherein the incidence angle (propagation angle) of the light L propagated through the core 63 is θ, and the thickness of the core 63 is T.

$$T = 2 \times T \times \tan \theta$$

Accordingly, the aforementioned condition is expressed as follows.

$$D > 2T \tan \theta$$

Accordingly, the collimate optical system 27 in the light projection portion 18 can be caused to collimate the light emitted from the light projection portion 18 and also to adjust the propagation angle θ within the core 63 to be a predetermined angle. However, in the case of an optical-waveguide type, the angle of propagated light is changed with the change of the refractive index of the material of the core 63 with respect to different wavelengths. In this case, the angle of light can be changed for respective wavelengths using the collimate optical system 27 (optical-path changing means) such that the propagation angle is maintained at the same value for all wavelengths when light enters the core 63.

Further, it is desirable that the thickness T of the core 63 is set to be the same as the thickness of a core in a normal multi-mode type optical waveguide, namely within the range of several micrometers to several hundreds of micrometers. However, if the thickness T of the core 63 is excessively large, the length D (>2T tan θ) of the determination areas 15a, 15b and 15c should be made greater and, therefore, it is desirable that the thickness T of the core 63 is several tens of micrometers.

For example, assuming that the incidence angle of the light L within the core 63 is 75 degree and the thickness of the core 63 is 50 micrometers, the length D of the determination areas 15a, 15b and 15c should be about 400 micrometers. Accordingly, when the three determination areas 15a, 15b and 15c are arranged in the single core 63, the length of the core 63 should be equal to or more than 1200 micrometers.

Further, usually, the core 63 is made of PMMA, the metal layer 13 is made of Au, and the dielectric layers 14a, 14b and 14c are made of $Ta_2O_5$, PMMA or polycarbonate. In this case, when normal biomolecules combine therewith, the characteristic wavelengths of signals are shifted by about 50 nm. Accordingly, by making the spacing ΔG between signal characteristic wavelengths to be equal to or more than 100 nm, it is possible to detect the characteristic wavelengths of signals with higher accuracy.

Further, the light receiving device 20 is required to cover all characteristic wavelengths. Namely, there is a need for a light receiving device 20 having a size and a number of cells which can receive light with wavelengths at least in the range of λ0 to λks with required resolution.

Figure 23:
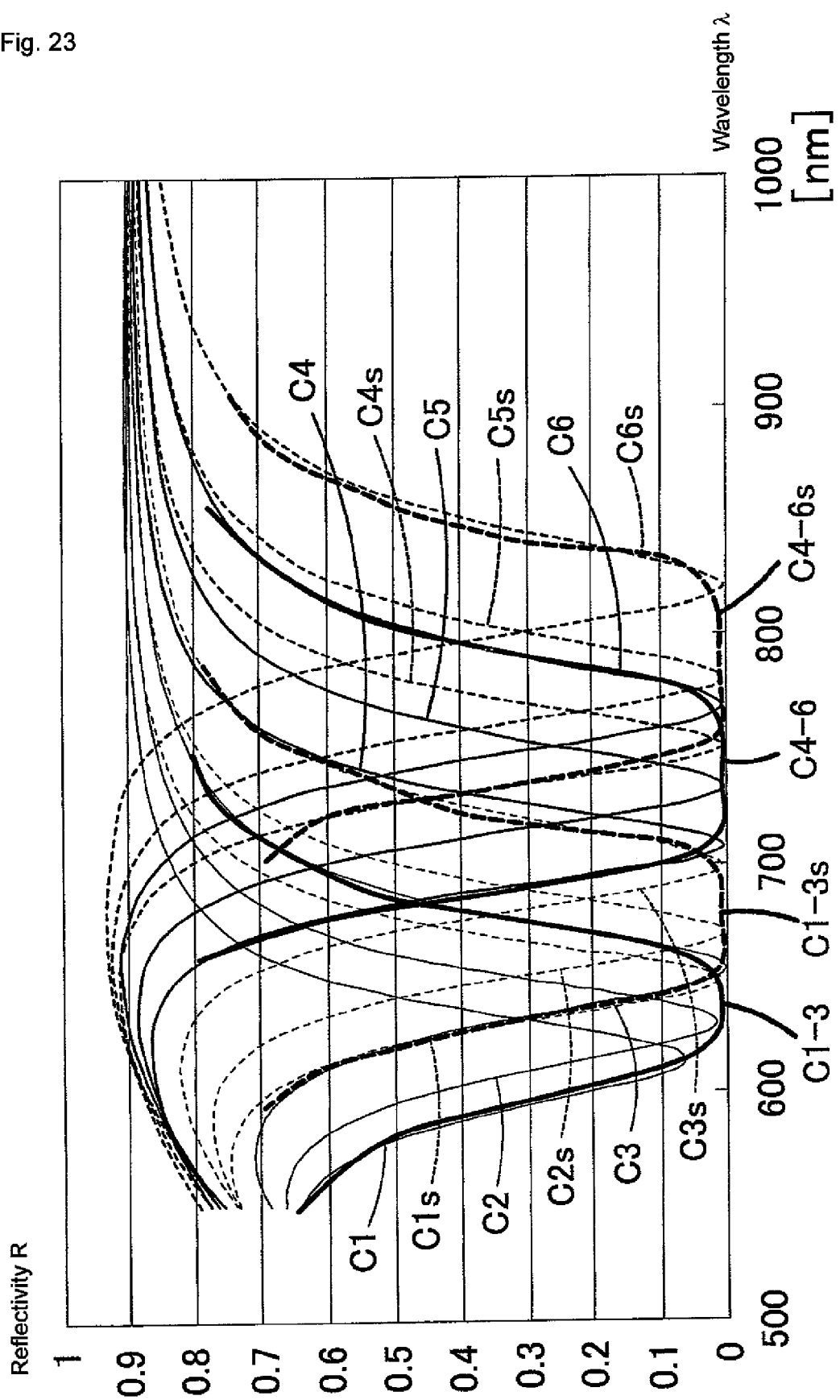
FIG. 23 is a view illustrating the results of simulations for characteristics, on the assumption that the divergence of light is ±2 degree and the thickness difference between dielectric layers is 10 nm.

Next, there will be described the influence of the divergence of the light emitted from the light projection portion 18. FIG. 23 illustrates the results of simulations for characteristics of an optical-waveguide-type surface plasmon resonance sensor, wherein the simulations were conducted on the assumption that the core was made of PMMA and had a refractive index of 1.492, the metal layer was made of Au and had a thickness of 50 nm, and dielectric layers with thicknesses of 0 nm and 10 nm made of $Ta_2O_5$ with a refractive index of 2.1 were formed on the metal layer. The characteristics C1, C2 and C3 in FIG. 23 represent characteristics of the dielectric layer with a thickness of 0 nm (only an antibody has been fixed and no antigen has not combined therewith) when light is incident to this dielectric layer at incidence angles of 73 degree, 75 degree and 77 degree. The characteristics C1s, C2s and C3s in FIG. 23 represent characteristics of the dielectric layer with a thickness of 0 nm after antigens with a size of, for example, 10 nm have combined with the antibody and thus the refractive index of the surface of this dielectric layer has been changed to 1.57 when light is incident to this dielectric layer at incident angles of 73 degree, 75 degree and 77 degree.

Similarly, the characteristics C4, C5 and C6 in FIG. 23 represent characteristics of the dielectric layer with a thickness of 10 nm (only an antibody has been fixed and no antigen has not combined therewith) when light is incident to this dielectric layer at incidence angles of 73 degree, 75 degree and 77 degree. Further, the characteristics C4s, C5s and C6s in FIG. 23 represent characteristics of the dielectric layer with a thickness of 10 nm after antigens with a size of, for example, 10 nm have combined with the antibody and thus the refractive index of the surface of this dielectric layer has been changed to 1.57 when light is incident to this dielectric layer at incident angles of 73 degree, 75 degree and 77 degree.

Accordingly, when light enters the dielectric layer with a thickness of 0 nm at an incidence angle of 75 degree with a divergence of ±2 degree, the dielectric layer with a thickness of 0 nm exhibits a characteristic C1-3 which is a composition of the characteristics C1, C2 and C3 before antigens combine therewith, and further, the dielectric layer with a thickness of 0 nm exhibits a characteristic C1-3s as a composition of the characteristics C1s, C2s and C3s after antigens combine therewith. Similarly, when light enters the dielectric layer with a thickness of 10 nm at an incidence angle of 75 degree with a divergence of ±2 degree, the dielectric layer with a thickness of 10 nm exhibits a characteristic C4-6 as a composition of the characteristics C1, C2 and C3 before antigens combine therewith and, further, the dielectric layer with a thickness of 10 nm exhibits a characteristic C4-6s as a composition of the characteristics C4s, C5s and C6s after antigens combine therewith.

From the results of simulations in FIG. 23, it is revealed that, when light with a divergence of ±2 degree is directed to the dielectric layer with a thickness of 10 nm, the characteristic wavelengths (ranges) of the respective characteristics C1-3, C1-3s, C4-6 and C4-6s have significant divergences. As a result, the characteristics C1-3 and C4-6 before antigens combine therewith and the characteristics C1-3s and C4-6s after antigens combine therewith are overlapped with one another, which makes it difficult to perform determinations. Further, the characteristics C1-3s and C4-6 of the dielectric layers with different thicknesses are also overlapped with one another, which makes it difficult to perform determinations.

Figure 24:
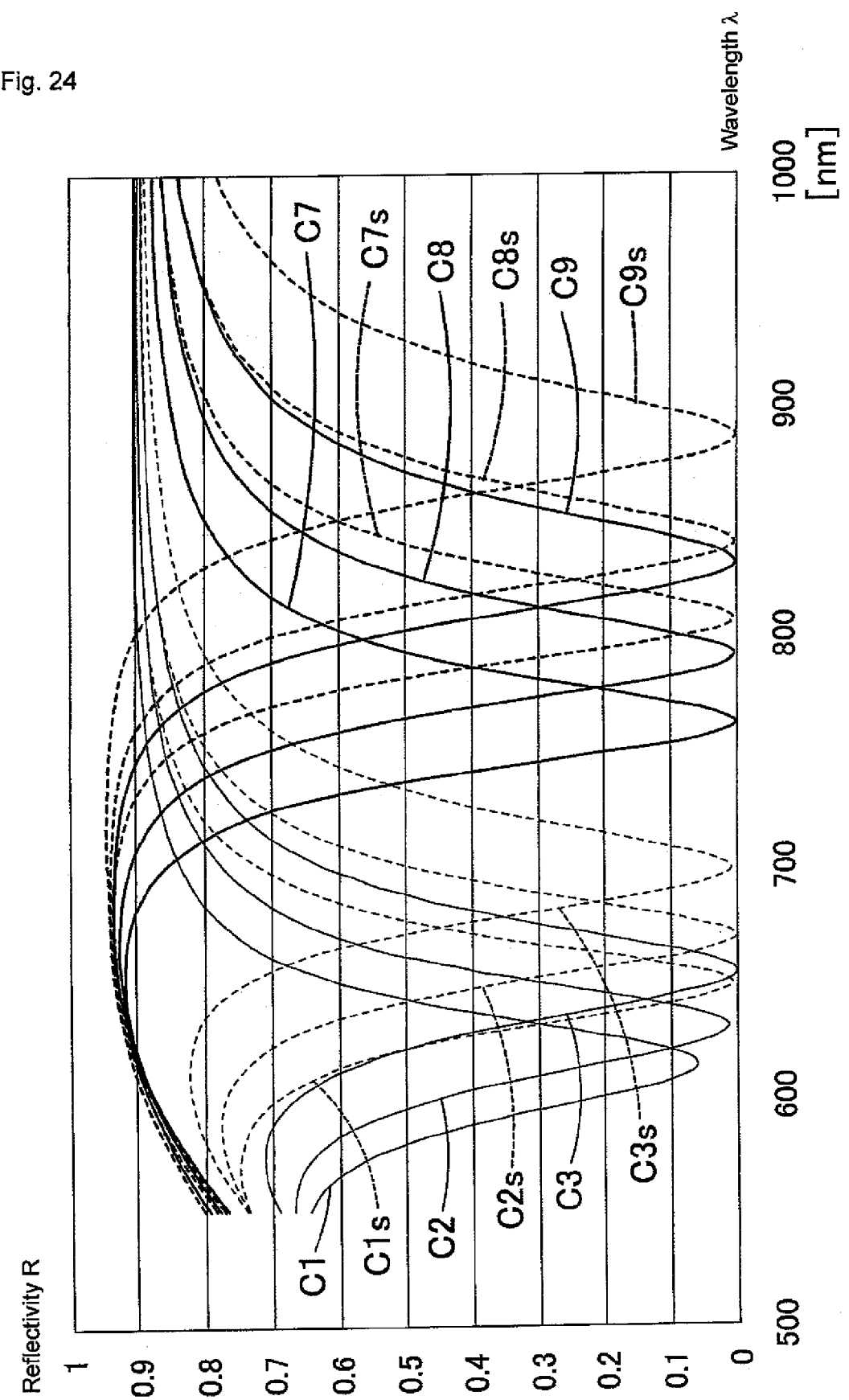
FIG. 24 is a view illustrating the results of simulations for characteristics, on the assumption that the divergence of light is ±2 degree and the thickness difference between dielectric layers is 15 nm.

Next, there will be described the results of simulations performed on the assumption that the divergence of light is ±2 degree and the thickness difference between dielectric layers is 15 nm. FIG. 24 illustrates the results of simulations for characteristics of an optical-waveguide-type surface plasmon resonance sensor, wherein the simulations were conducted on the assumption that the core was made of PMMA and had a refractive index of 1.492, the metal layer was made of Au and had a thickness of 50 nm, and dielectric layers with thicknesses of 0 nm and 15 nm made of $Ta_2O_5$ with a refractive index of 2.1 were formed on the metal layer. The characteristics C1, C2 and C3 in FIG. 24 represent characteristics of the dielectric layer with a thickness of 0 nm (only an antibody has been fixed and no antigen has not combined therewith) when light is incident to this dielectric layer at incidence angles of 73 degree, 75 degree and 77 degree. The characteristics C1s, C2s and C3s in FIG. 24 represent characteristics of the dielectric layer with a thickness of 0 nm after antigens with a size of, for example, 10 nm have combined with the antibody and thus the refractive index of the surface of this dielectric layer has been changed to 1.57 when light is incident to this dielectric layer at incident angles of 73 degree, 75 degree and 77 degree.

Similarly, the characteristics C7, C8 and C9 in FIG. 24 represent characteristics of the dielectric layer with a thickness of 15 nm (only an antibody has been fixed and no antigen has not combined therewith) when light is incident to this dielectric layer at incidence angles of 73 degree, 75 degree and 77 degree. Further, the characteristics C7s, C8s and C9s in FIG. 24 represent characteristics of the dielectric layer with a thickness of 15 nm after antigens with a size of, for example, 10 nm have combined with the antibody and thus the refractive index of the surface of this dielectric layer has been changed to 1.57 when light is incident to this dielectric layer at incident angles of 73 degree, 75 degree and 77 degree.

From the results of simulations of FIG. 24, it is revealed that, when light with a divergence of ±2 degree is directed to the dielectric layers having thicknesses different from one another by 15 nm, there is no overlap between the characteristics C1 to C3, C1s to C3s and C7 to C9, C7s to C9s of the dielectric layers having the different thicknesses. However, there is an overlap between the characteristics before reactions and the characteristics after reactions (for example, between C3 and C1s, and between C9 and C8), which makes it difficult to perform determinations. However, when the intensity distribution of the light emitted from the light projection portion 18 is a normal distribution centered about the direction along the front surface, it may be possible to perform sensing, although the widths of signals can be increased, thereby reducing the sensitivity.

Figure 25:
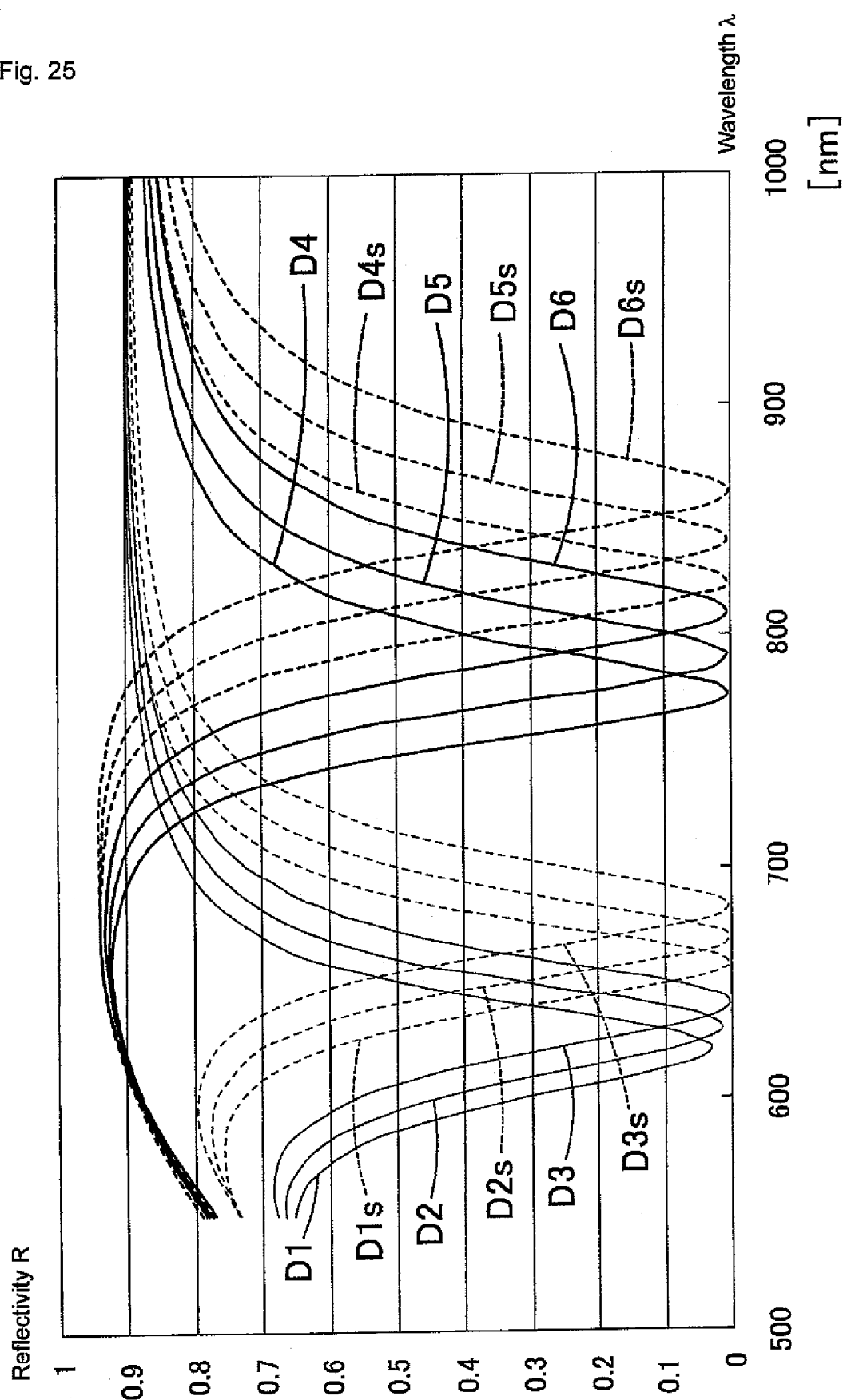
FIG. 25 is a view illustrating the results of simulations for characteristics, on the assumption that the divergence of light is ±1 degree and the thickness difference between dielectric layers is 15 nm.

Next, there will be described the results of simulations performed on the assumption that the divergence of light is ±1 degree and the thickness difference between dielectric layers is 15 nm. FIG. 25 illustrates the results of simulations for characteristics of an optical-waveguide-type surface plasmon resonance sensor, wherein the simulations were conducted on the assumption that the core was made of PMMA and had a refractive index of 1.492, the metal layer was made of Au and had a thickness of 50 nm, and dielectric layers with thicknesses of 0 nm and 15 nm made of $Ta_2O_5$ with a refractive index of 2.1 were formed on the metal layer. The characteristics D1, D2 and D3 in FIG. 25 represent characteristics of the dielectric layer with a thickness of 0 nm (only an antibody has been fixed and no antigen has not combined therewith) when light is incident to this dielectric layer at incidence angles of 74 degree, 75 degree and 76 degree. The characteristics D1s, D2s and D3s in FIG. 25 represent characteristics of the dielectric layer with a thickness of 0 nm after antigens with a size of, for example, 10 nm have combined with the antibody and thus the refractive index of the surface of this dielectric layer has been changed to 1.57 when light is incident to this dielectric layer at incident angles of 74 degree, 75 degree and 76 degree.

Similarly, the characteristics D4, D5 and D6 in FIG. 25 represent characteristics of the dielectric layer with a thickness of 15 nm (only an antibody has been fixed and no antigen has not combined therewith) when light is incident to this dielectric layer at incidence angles of 74 degree, 75 degree and 76 degree. Further, the characteristics D4s, D5s and D6s in FIG. 25 represent characteristics of the dielectric layer with a thickness of 15 nm after antigens with a size of, for example, 10 nm have combined with the antibody and thus the refractive index of the surface of this dielectric layer has been changed to 1.57 when light is incident to this dielectric layer at incident angles of 74 degree, 75 degree and 76 degree.

From the results of simulations of FIG. 25, it is revealed that, when light with a divergence of ±1 degree is directed to the dielectric layers having thicknesses different from one another by 15 nm, it is possible to maintain the independence of characteristic wavelengths, which makes it possible to perform determinations.

According to the results of simulations of FIGS. 23 to 25, when the light emitted from the light projection portion has a divergence angle, it is desirable to make the divergence angle of the light to be equal to or less than 1 degree, in order to maintain the independence. Further, it is desirable to set the thickness difference between the dielectric layers to be equal to or more than 15 nm. Further, in assuming that the wavelength sensitivity of the light receiving device is in the range of 500 nm to 1000 nm, the number of determination areas should be 2 and, in this case, one of the determination areas can be used for reference for correcting the variations of determinations.

FIFTH EXAMPLE

Figure 26:
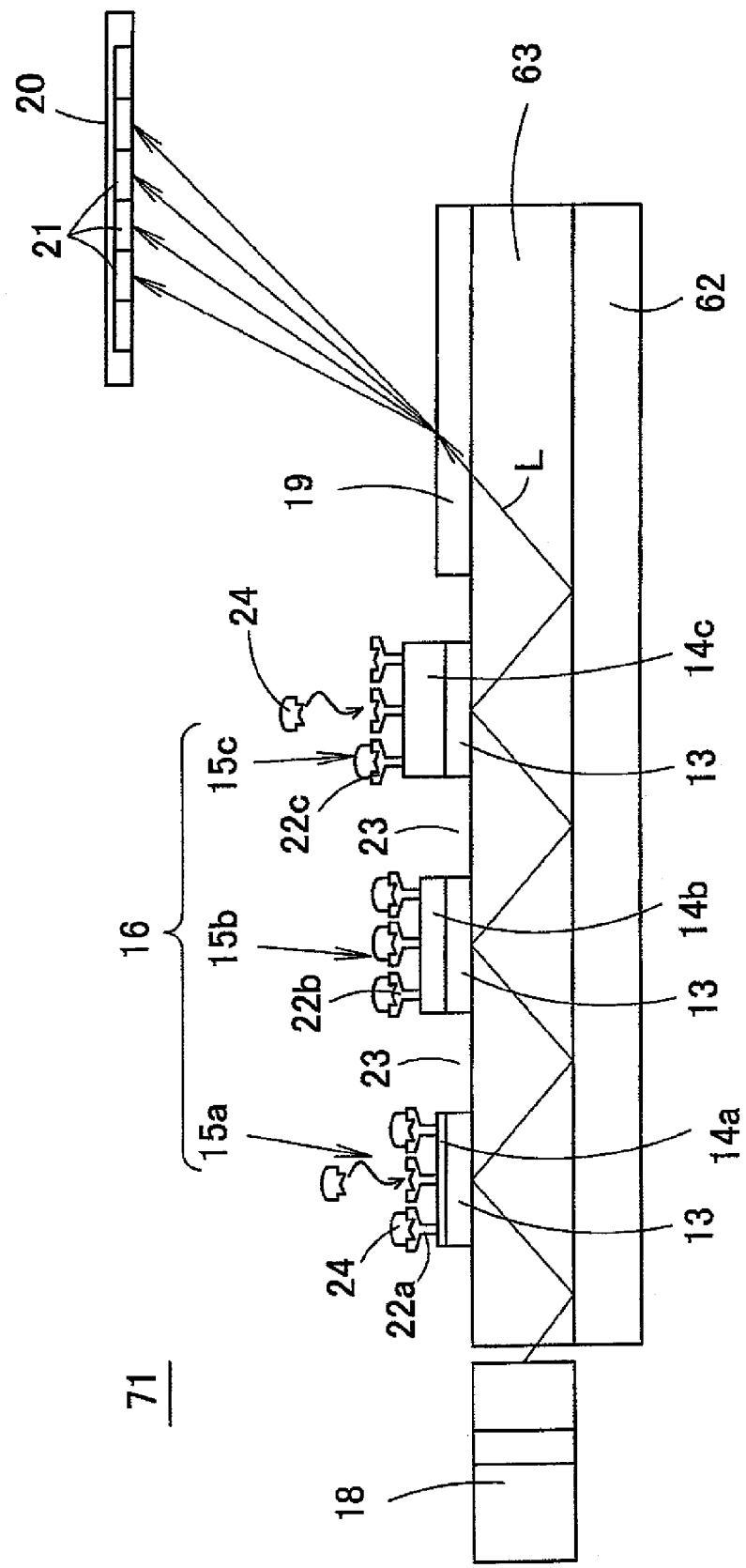
FIG. 26 is a side view illustrating a surface plasmon resonance sensor according to a fifth example of the present invention.

FIG. 26 is a side view illustrating a surface plasmon resonance sensor 71 according to a fifth example of the present invention. In the fourth example, the metal layer 13 is formed in the areas outside of the determination areas 15a, 15b and 15c, but, in the surface plasmon resonance sensor 71 according to the fifth example, a metal layer 13 is not provided in the areas outside of the determination areas 15a, 15b and 15c. Accordingly, a core 63 is exposed at the areas outside of the determination areas 15a, 15b and 15c, which enables applying hydrophilic processing or hydrophobic processing to the areas (the upper surfaces of a clad 62 and the core 63) other than the determination areas 15a, 15b and 15c for preventing antigens from nonspecifically combining with the areas other than the determination areas 15a, 15b and 15c, which can reduce signal noises due to unnecessary antigens, thereby increasing the determination accuracy.

SIXTH EXAMPLE

Figure 27:
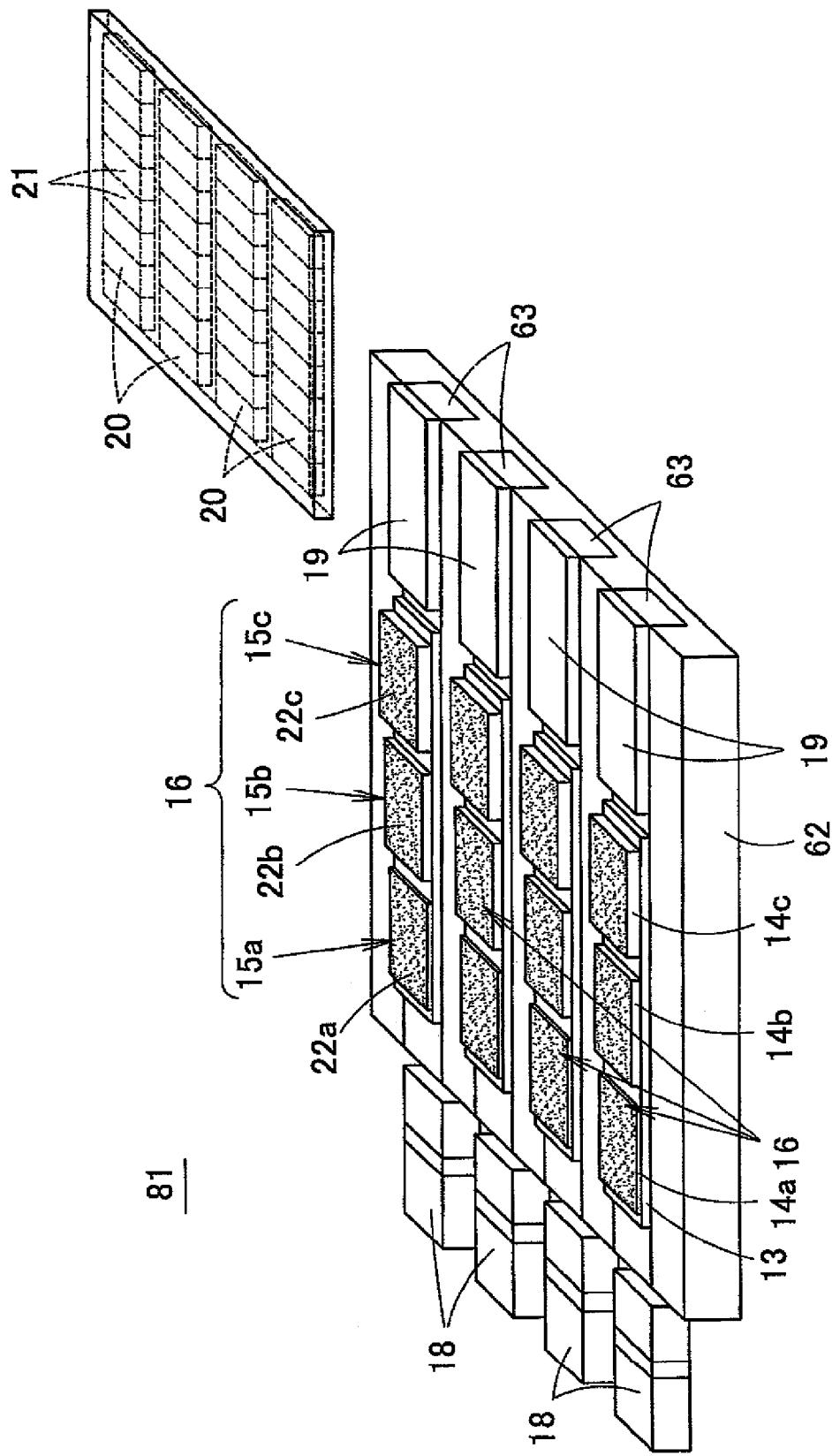
FIG. 27 is a perspective view illustrating a surface plasmon resonance sensor according to a sixth example of the present invention.
Figure 28:
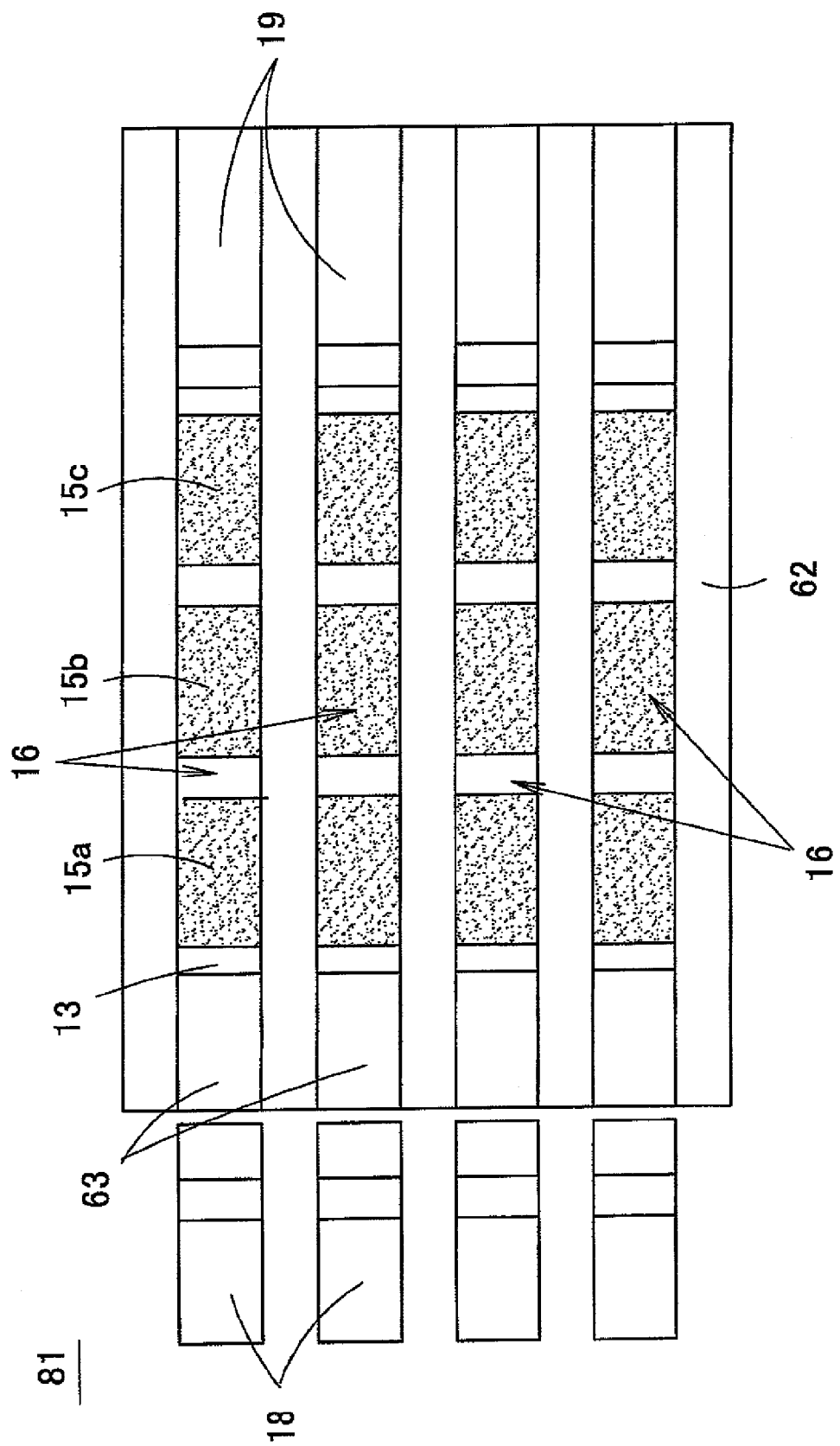
FIG. 28 is a plan view illustrating a surface plasmon resonance sensor 81 according to a sixth example of the present invention.

FIG. 27 is a perspective view illustrating a surface plasmon resonance sensor 81 according to a sixth example of the present invention. FIG. 28 is a plan view of the same. In the surface plasmon resonance sensor 81 according to the sixth example, a plurality of cores 63 are provided, and a sample detection portion 16 constituted by a plurality of determination areas 15a, 15b and 15c and a light dispersion means 19 are arranged on each core 63. Further, although not illustrated, a number of light receiving devices 20 corresponding to the number of cores 63 are provided thereon.

Thus, spectral characteristics of light L reflected by the respective sample detection portions 16 are individually detected by the respective light receiving devices 20, which enables the surface plasmon resonance sensor 81 according to the six example to perform an extremely greater number of inspections (12(=3×4) types of inspections) at one time, thereby significantly increasing the inspection efficiency. However, the number of cores 63 and the number of determination areas are not limited to those illustrated in the figure.

Figure 29:
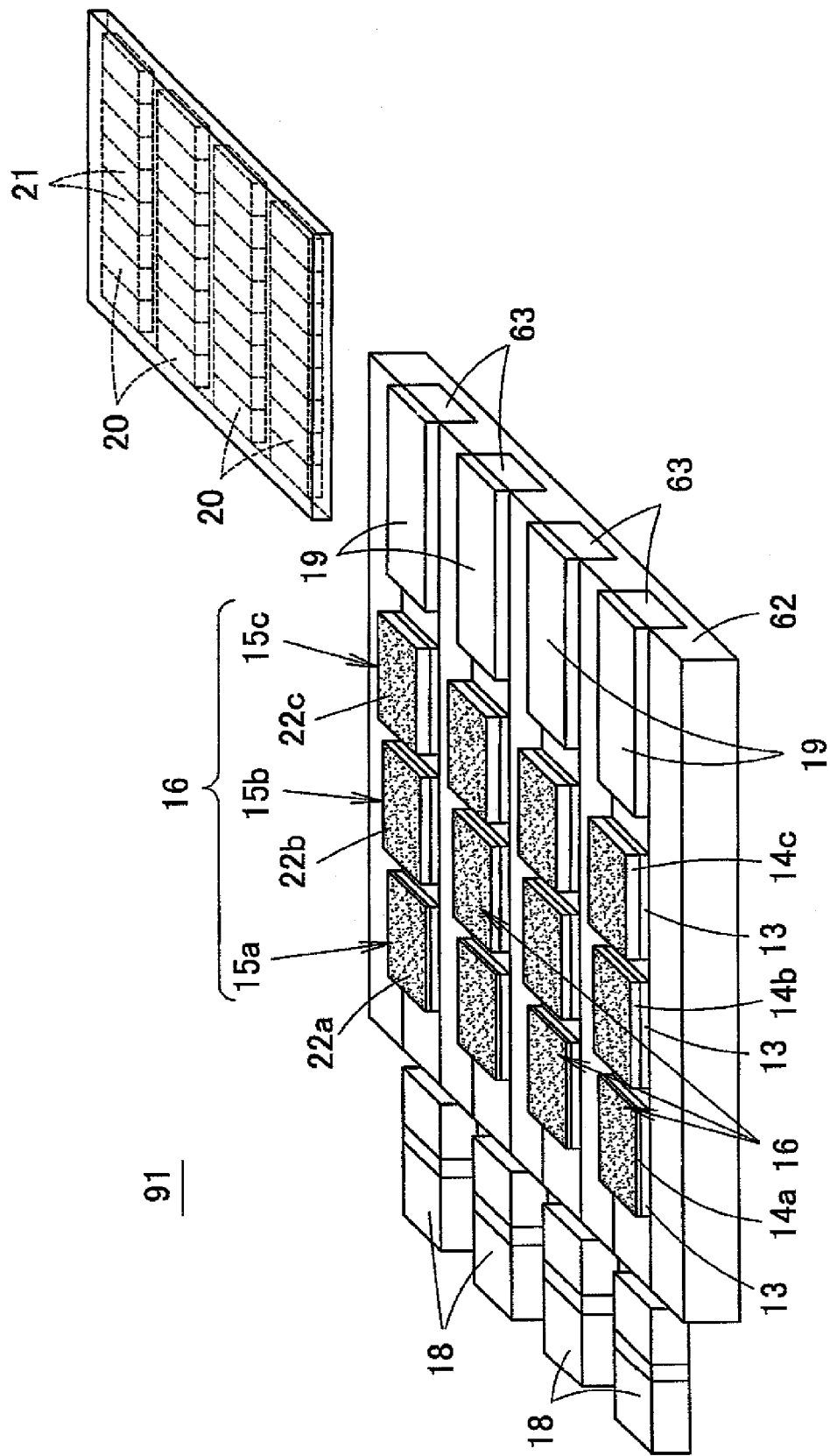
FIG. 29 is a perspective view illustrating a surface plasmon resonance sensor according to a modified example of the fifth example of the present invention.

Further, in the example, similarly, as in the surface plasmon resonance sensor 91 illustrated in FIG. 29, the metal layer 13 can be removed at the areas other than the determination areas 15a, 15b and 15c, in order to enable applying hydrophilic processing or hydrophobic processing to the areas outside of the determination areas 15a, 15b and 15c at which the core 63 and the like are exposed for preventing antigens from nonspecifically combining therewith.

SEVENTH EXAMPLE

Figure 30:
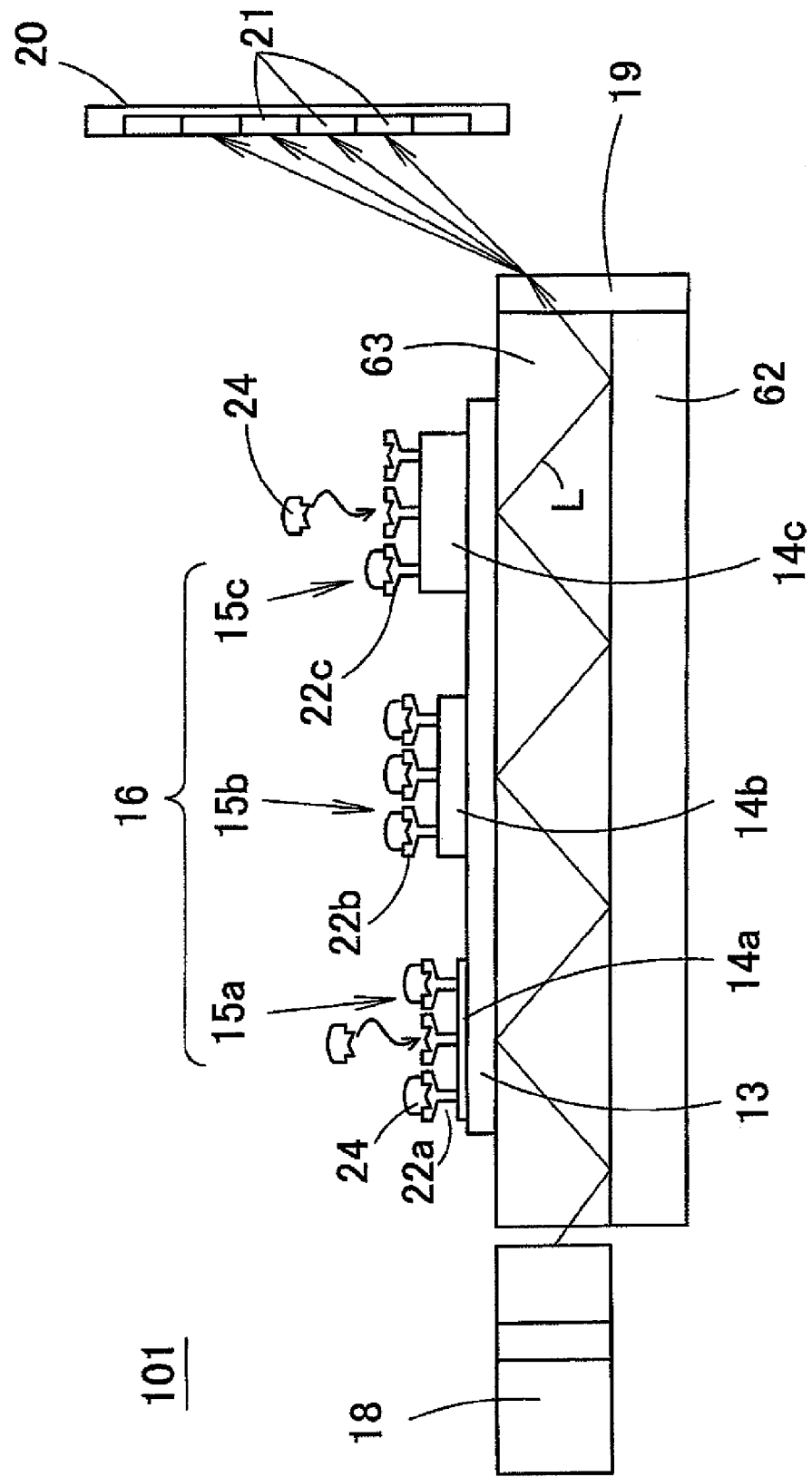
FIG. 30 is a side view illustrating a surface plasmon resonance sensor according to a seventh example of the present invention.

FIG. 30 is a side view of a surface plasmon resonance sensor 101 according to a seventh example of the present invention. The surface plasmon resonance sensor 101 according to the seventh example is adapted such that light propagated through a core 63 is emitted from the end surface of the core 63 opposite from a light projection portion 18, and a light dispersion means 19 is provided at this end surface for dispersing the light L, and a light receiving device 20 placed vertically near the light dispersion means 19 receives signals.

EIGHTH EXAMPLE

Figure 31:
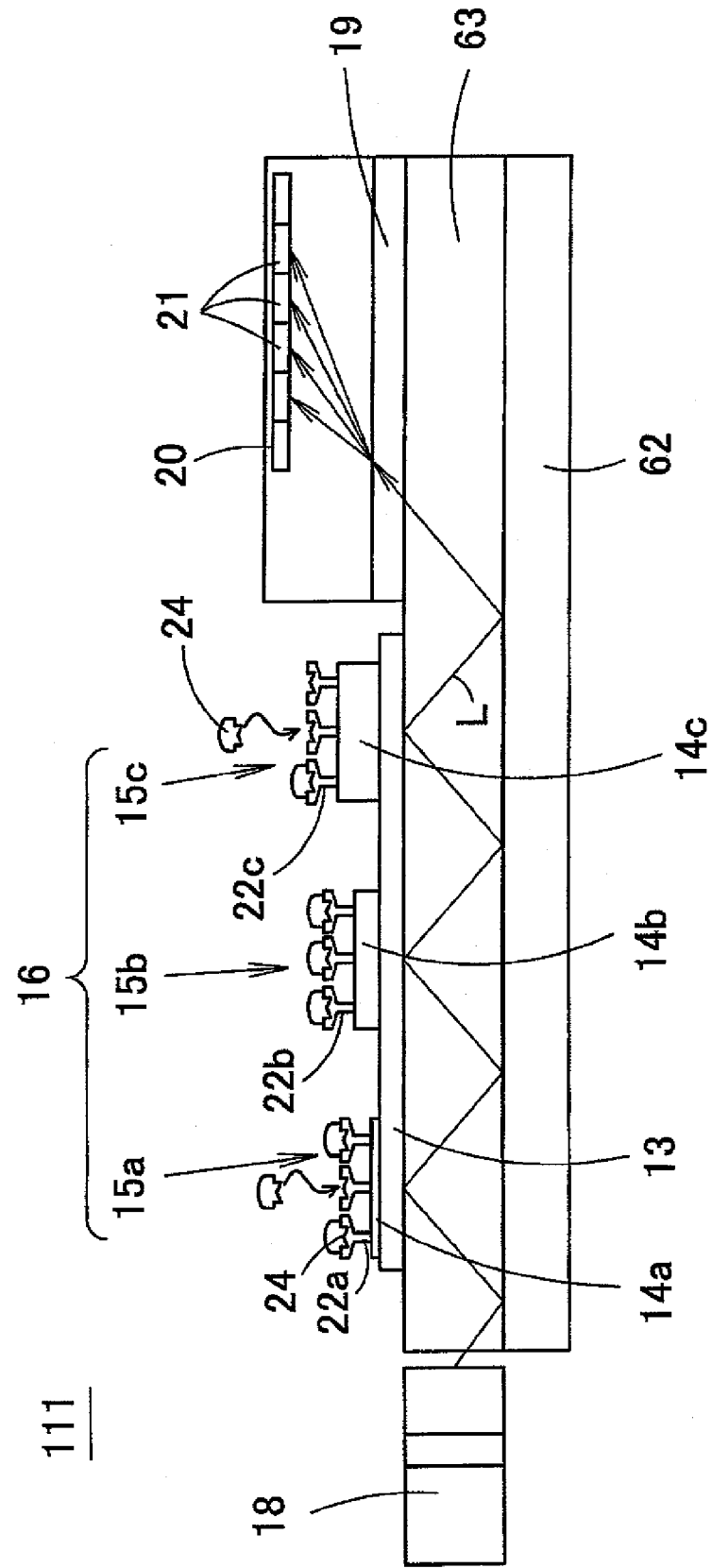
FIG. 31 is a side view illustrating a surface plasmon resonance sensor according to an eighth example of the present invention.

FIG. 31 is a side view illustrating a surface plasmon resonance sensor 111 according to a ninth example of the present invention. The surface plasmon resonance sensor 111 according to the ninth example includes a light receiving device 20 and a light dispersion means 19 provided on the upper surface of an end portion of a core 63, the light receiving device 20 and the light dispersion means 19 being integral with each other.

Further, while, in the aforementioned respective examples, there have been illustrated cases of utilizing antigen-antibodies reactions, the examples of the present invention can be utilized for determinations and observations of any biomolecules such as DNAs, RNAs, proteins, sugar chains, as well as antigens and antibodies.

NINTH EXAMPLE

Figure 32:
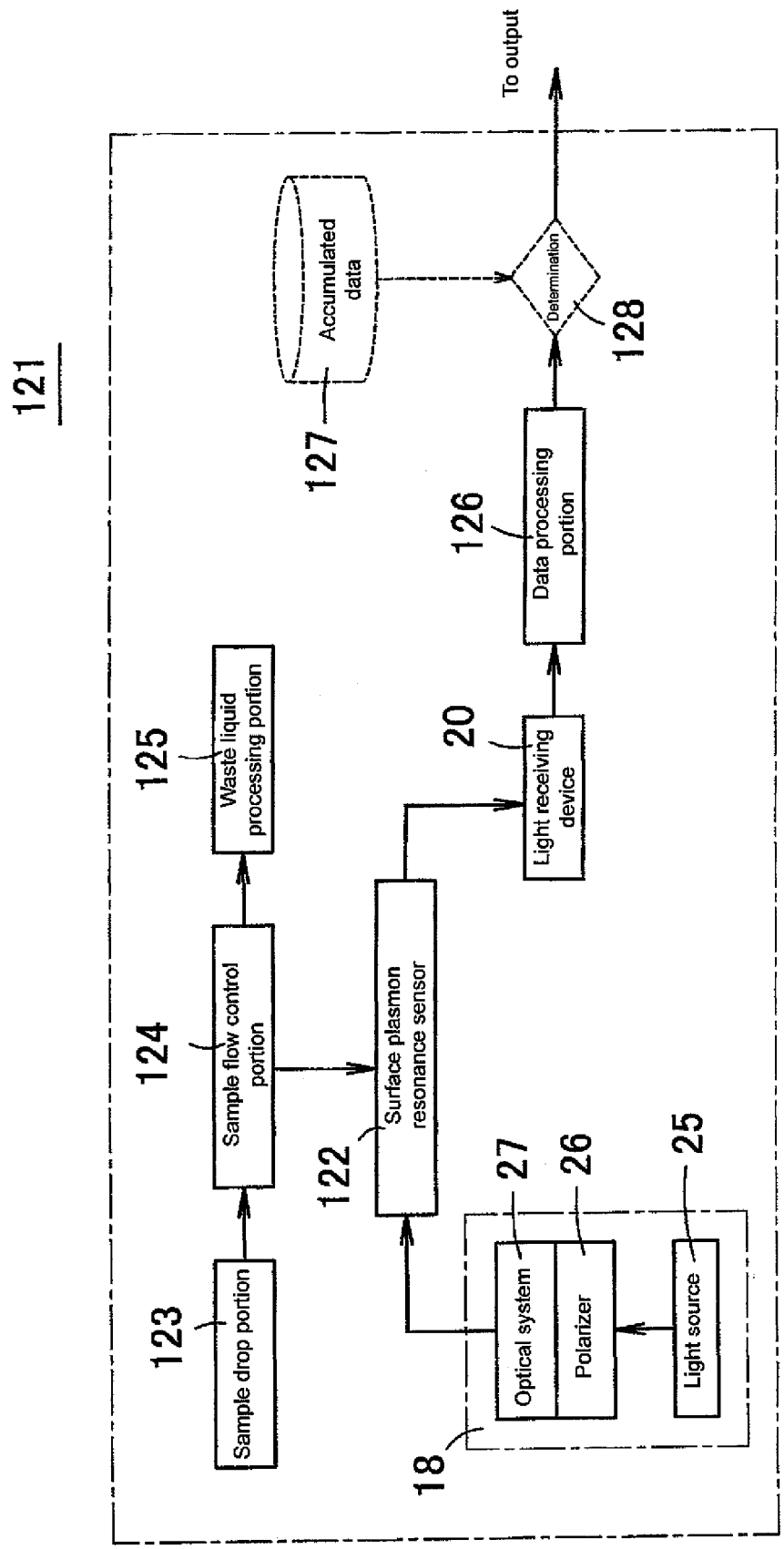
FIG. 32 is a block diagram illustrating the structure of an inspection apparatus using a surface plasmon resonance sensor according to the present invention.

FIG. 32 is a block diagram illustrating the structure of an inspection apparatus 121 using a surface plasmon resonance sensor 122 according to the present invention. The inspection apparatus 121 can be used as either a medical inspection apparatus or a chemical material inspection apparatus, depending on objects to be inspected. In the case of using the inspection apparatus 121 as a medical inspection apparatus, a material with biomolecule recognition function which specifically combines with a certain biomolecule is fixed on dielectric layers. In the case of using the inspection apparatus 121 as a chemical inspection apparatus, a material having chemical-material recognition function which combines with a certain chemical material can be fixed on dielectric layers.

The inspection apparatus 121 has a structure for transferring samples to the sample plasmon resonance sensor 122, in addition to the structure of the surface plasmon resonance sensor 122. Namely, after preparing the surface plasmon resonance sensor 122 having a predetermined material having biomolecular recognition function fixed thereto, a sample solution is dropped onto a sample drop portion 123. Then, the sample solution dropped onto the sample drop portion 123 is supplied to the surface plasmon resonance sensor 122 at a constant flow rate through a sample flow control portion 124 such as a pump and, then, the inspected sample solution which has passed through respective determination areas in the surface plasmon resonance sensor 122 is transferred to a waste-liquid processing portion 125 and is collected therein.

On the other hand, in the surface plasmon resonance sensor 122, a light projection portion 18 emits light to the determination areas, and a light receiving device 20 receives light completely reflected by the determination areas and then outputs inspection data.

The surface plasmon resonance sensor 122 outputs a spectral characteristic of the sample solution as inspection data to a data processing portion 126. This data is stored in a storage device 127 through a determination processing portion 128, and the result of the determination by the determination processing portion 128 is output to an external output device. Also, the storage device 127 and the determination processing portion 128 can be eliminated.

With the inspection apparatus 121, it is possible to perform analyses of SNP (Single Nucleotide polymorphism), determination of paths or states of metabolism, absorption and evacuation of materials administered to experiment mice, determination of ion concentrations of cells, identification of proteins or analyses of functions of proteins, and the like, as well as antigen-antibody reactions. Furthermore, the inspection apparatus 121 can also be used for medical checkup for determining medical conditions of individual persons and inspections for personal securities.

The invention claimed is:

1. A surface plasmon resonance sensor chip comprising:
   a substrate;
   a plurality of metal layers placed such that the plurality of metal layers are spaced apart from one another by a predetermined distance on the upper surface of said substrate; and
   a dielectric layer formed on each of said metal layers,
   wherein at least portions of a plurality of said dielectric layers have thicknesses different from one another; and
   wherein each of the metal layers has substantially the same area as that of the dielectric layer formed thereon.

2. The surface plasmon resonance sensor chip according to claim 1, wherein a prism is intimately contacted with the lower surface of said substrate.

3. The surface plasmon resonance sensor chip according to claim 1, comprising a plurality of sample detection portions including a plurality of said dielectric layers having different thicknesses formed on the upper surface of said metal layer.

4. A surface plasmon resonance sensor chip comprising:
an optical waveguide having a core formed therein;
determination areas formed on said core; and
a light dispersion means for dispersing light which has been propagated through said core and reflected by said determination areas;
wherein said determination areas include a plurality of metal layer layers placed such that the plurality of metal layers are spaced apart from one another by a predetermined distance on said core, and a dielectric layer formed on each of said metal layers;
wherein at least portions of a plurality of said dielectric layers have thicknesses different from one another; and
wherein each of the metal layers has substantially the same area as that of the dielectric layer formed thereon.

5. The surface plasmon resonance sensor chip according to claim 4, wherein said optical waveguide comprises a plurality of said cores formed therein, and said determination areas are formed on the respective cores.

6. The surface plasmon resonance sensor chip according to claim 4, wherein the length D of said respective dielectric layers in a core longitudinal direction is expressed as follows, $D \geq 2 \times T \times \tan\theta$ wherein T is a thickness of said core, and $\theta$ is the incidence angle at which light propagated through the core enters said determination areas.

7. The surface plasmon resonance sensor chip according to claim 4, wherein said light dispersion means is provided at a portion of said core, and there is provided a light receiving device comprising a plurality of light receiving areas which receive light with different wavelengths resulted from the light dispersion by said light dispersion means.

8. The surface plasmon resonance sensor chip according to claim 4, wherein different molecule-recognition-function materials are fixed to said respective determination areas.

9. The surface plasmon resonance sensor chip according to claim 1, wherein said dielectric layers have thicknesses different from one another by 10 nm or more.

10. The surface plasmon resonance sensor chip according to claim 1, wherein said metal layer is made of Au, Ag or Cu.

11. The surface plasmon resonance sensor chip according to claim 1, wherein said dielectric layers are made of a material with a high dielectric constant.

12. The surface plasmon resonance sensor chip according to claim 1, wherein said dielectric layers are made of $Ta_2O_5$ or $TiO_2$.

13. The surface plasmon resonance sensor chip according to claim 1, wherein said dielectric layers are made of a resin with a high refractive index.

14. A method for fabricating the surface plasmon resonance sensor chip according to claim 1, wherein a dielectric resin material is provided on said metal layer, and then the dielectric resin material is pressed by a die having a plurality of concave portions with different depths formed therein to form a plurality of dielectric layers having different thicknesses from said dielectric resin material.

15. A method for fabricating the surface plasmon resonance sensor according to claim 1, comprising the steps of:
providing a dielectric resin material on said metal layer, and pressing the dielectric resin material by a die having a plurality of concave portions with different depths formed therein to form a plurality of dielectric layers having different thicknesses from said dielectric resin material; and
removing, through etching, the portions of the metal layer which are exposed through said dielectric layers.

16. The surface plasmon resonance sensor chip according to claim 4, wherein said dielectric layers have thicknesses different from one another by 10 nm or more.

17. The surface plasmon resonance sensor chip according to claim 4, wherein said metal layer is made of Au, Ag or Cu.

18. The surface plasmon resonance sensor chip according to claim 4, wherein said dielectric layers are made of a material with a high dielectric constant.

19. The surface plasmon resonance sensor chip according to claim 4, wherein said dielectric layers are made of $Ta_2O_5$ or $TiO_2$.

20. The surface plasmon resonance sensor chip according to claim 4, wherein said dielectric layers are made of a resin with a high refractive index.

21. A method for fabricating the surface plasmon resonance sensor chip according to claim 4, wherein a dielectric resin material is provided on said metal layer, and then the dielectric resin material is pressed by a die having a plurality of concave portions with different depths formed therein to form a plurality of dielectric layers having different thicknesses from said dielectric resin material.

22. A method for fabricating the surface plasmon resonance sensor according to claim 4, comprising the steps of:
providing a dielectric resin material on said metal layer, and pressing the dielectric resin material by a die having a plurality of concave portions with different depths formed therein to form a plurality of dielectric layers having different thicknesses from said dielectric resin material; and
removing, through etching, the portions of the metal layer which are exposed through said dielectric layers.

* * * * *